United States Patent
Mazanec

(10) Patent No.: US 12,151,102 B2
(45) Date of Patent: *Nov. 26, 2024

(54) COMBINATION HEARING AID AND COCHLEAR IMPLANT SYSTEM

(71) Applicant: Envoy Medical Corporation, White Bear Lake, MN (US)

(72) Inventor: Paul R. Mazanec, Ham Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/324,538

(22) Filed: May 26, 2023

(65) Prior Publication Data
US 2023/0293888 A1    Sep. 21, 2023

Related U.S. Application Data

(63) Continuation of application No. 17/109,304, filed on Dec. 2, 2020, now Pat. No. 11,697,019.

(51) Int. Cl.
*A61N 1/36* (2006.01)
*A61N 1/05* (2006.01)
(Continued)

(52) U.S. Cl.
CPC ....... *A61N 1/36038* (2017.08); *A61N 1/0541* (2013.01); *A61N 1/36146* (2013.01);
(Continued)

(58) Field of Classification Search
CPC .............. A61N 1/36038; A61N 1/0541; A61N 1/36146; A61N 1/37223; A61N 1/37235;
(Continued)

(56) References Cited

U.S. PATENT DOCUMENTS

| | | |
|---|---|---|
| 2,827,041 A | 3/1958 | Pierson |
| 4,400,590 A | 8/1983 | Michelson |
| (Continued) | | |

FOREIGN PATENT DOCUMENTS

| | | |
|---|---|---|
| CN | 104394930 A | 3/2015 |
| CN | 110086237 A | 8/2019 |
| (Continued) | | |

OTHER PUBLICATIONS

PCT International Search Report and Written Opinion dated Mar. 14, 2022 for related Intl. App. No. PCT/US2021/060713, 9 pages.

*Primary Examiner* — Catherine M Voorhees
(74) *Attorney, Agent, or Firm* — Fredrikson & Byron, P.A.

(57) ABSTRACT

Cochlear implant systems can comprise a cochlear implant system comprising a cochlear electrode, a stimulator, an input source, and an implantable battery and/or communication module. The signal processor may be programmed with a transfer function and be configured to receive input signals from the input source and output a stimulation signal to the stimulator based on the received input signals with the transfer function. The system may be configured to receive a status indicator signal indicative of whether an external auditory aid device is active and update the transfer function of the signal processor if the external auditory aid device is active. For example, the signal processor can operate programmed with a first transfer function if the external auditory aid device is not active and with a second transfer function if the external auditory aid device is active.

20 Claims, 11 Drawing Sheets

(51) Int. Cl.
*A61N 1/372* (2006.01)
*A61N 1/378* (2006.01)
*H04R 25/00* (2006.01)

(52) U.S. Cl.
CPC ..... *A61N 1/37223* (2013.01); *A61N 1/37235* (2013.01); *A61N 1/378* (2013.01); *H04R 25/554* (2013.01); *H04R 25/606* (2013.01); *H04R 2225/43* (2013.01); *H04R 2225/55* (2013.01); *H04R 2225/67* (2013.01)

(58) Field of Classification Search
CPC .. A61N 1/378; A61N 1/36039; H04R 25/554; H04R 25/606; H04R 2225/43; H04R 2225/55; H04R 2225/67; H04R 25/70; A61B 5/4851; A61B 5/6817
See application file for complete search history.

(56) References Cited

U.S. PATENT DOCUMENTS

| | | | |
|---|---|---|---|
| 4,495,384 | A | 1/1985 | Scott et al. |
| 4,729,366 | A | 3/1988 | Schaefer |
| 4,850,962 | A | 7/1989 | Schaefer |
| 4,918,745 | A | 4/1990 | Hutchison |
| 5,540,095 | A | 7/1996 | Sherman et al. |
| 5,755,742 | A | 5/1998 | Schuelke et al. |
| 5,762,583 | A | 6/1998 | Adams et al. |
| 6,195,585 | B1 | 2/2001 | Karunasiri et al. |
| 6,212,431 | B1 | 4/2001 | Hahn et al. |
| 6,259,951 | B1 | 7/2001 | Kuzma et al. |
| 6,272,382 | B1 | 8/2001 | Faltys et al. |
| 6,308,101 | B1 | 10/2001 | Faltys et al. |
| 6,358,281 | B1 | 3/2002 | Berrang et al. |
| 6,391,024 | B1 | 5/2002 | Sun et al. |
| 6,754,537 | B1 | 6/2004 | Harrison et al. |
| 7,225,028 | B2 | 5/2007 | Della Santina et al. |
| 7,319,906 | B2 | 1/2008 | Kuzma et al. |
| 7,376,563 | B2 | 5/2008 | Leysieffer et al. |
| 7,524,278 | B2 | 4/2009 | Madsen et al. |
| 7,729,775 | B1 | 6/2010 | Saoji et al. |
| 8,233,651 | B1 | 7/2012 | Haller |
| 8,554,329 | B1 | 10/2013 | Mann et al. |
| 8,626,308 | B2 | 1/2014 | Meskens |
| 8,655,449 | B2 | 2/2014 | Haller et al. |
| 8,855,324 | B2 | 10/2014 | Franck |
| 8,942,815 | B2 | 1/2015 | Chung et al. |
| 8,954,158 | B2 | 2/2015 | Smith |
| 9,061,140 | B2 | 6/2015 | Shi et al. |
| 9,205,272 | B2 | 12/2015 | Suaning et al. |
| 9,511,225 | B2 | 12/2016 | Milczynski et al. |
| 9,693,155 | B2 | 6/2017 | Meister et al. |
| 9,716,952 | B2 | 7/2017 | Mauger |
| 9,775,999 | B2 | 10/2017 | Chalupper |
| 9,993,644 | B2 | 6/2018 | Koka et al. |
| 9,999,770 | B2 | 6/2018 | Walraevens et al. |
| 10,015,603 | B2 | 7/2018 | Sabin |
| 10,970,030 | B2 | 4/2021 | Guetta et al. |
| 10,994,126 | B2 | 5/2021 | Francart et al. |
| 11,324,958 | B2 | 5/2022 | Anderson et al. |
| 11,697,019 | B2* | 7/2023 | Mazanec ............ A61N 1/37223 607/57 |
| 2002/0015506 | A1 | 2/2002 | Aceti et al. |
| 2002/0039425 | A1 | 4/2002 | Burnett et al. |
| 2002/0099421 | A1 | 7/2002 | Goldsmith et al. |
| 2004/0230254 | A1 | 11/2004 | Harrison et al. |
| 2005/0033384 | A1 | 2/2005 | Sacha |
| 2005/0197677 | A1 | 9/2005 | Stevenson |
| 2006/0122664 | A1 | 6/2006 | Sacha et al. |
| 2006/0183965 | A1 | 8/2006 | Kasic et al. |
| 2008/0195179 | A1 | 8/2008 | Quick |
| 2008/0300658 | A1 | 12/2008 | Meskens |
| 2009/0018616 | A1 | 1/2009 | Quick et al. |
| 2009/0082831 | A1 | 3/2009 | Paul et al. |
| 2009/0171421 | A1 | 7/2009 | Atalar et al. |
| 2009/0187233 | A1 | 7/2009 | Stracener |
| 2009/0192565 | A1 | 7/2009 | Lee et al. |
| 2010/0010582 | A1 | 1/2010 | Carbunaru et al. |
| 2010/0030012 | A1 | 2/2010 | Meskens |
| 2010/0042183 | A1 | 2/2010 | Beck |
| 2010/0317913 | A1 | 12/2010 | Conn et al. |
| 2011/0082521 | A1 | 4/2011 | Botros et al. |
| 2011/0098785 | A1* | 4/2011 | Mishra ............... A61N 1/36038 607/57 |
| 2011/0116669 | A1 | 5/2011 | Karunasiri |
| 2011/0137180 | A1 | 6/2011 | Johnson et al. |
| 2011/0144719 | A1 | 6/2011 | Perkins et al. |
| 2011/0160808 | A1 | 6/2011 | Lyden et al. |
| 2011/0190568 | A1 | 8/2011 | Van Den Heuvel |
| 2011/0280426 | A1 | 11/2011 | Bachler |
| 2011/0295331 | A1 | 12/2011 | Wells et al. |
| 2012/0063610 | A1 | 3/2012 | Kaulberg et al. |
| 2012/0215285 | A1 | 8/2012 | Tahmasian et al. |
| 2012/0277835 | A1 | 11/2012 | Della Santina et al. |
| 2013/0018216 | A1 | 1/2013 | Beckerle et al. |
| 2013/0023953 | A1 | 1/2013 | Van Den Honert |
| 2013/0193914 | A1 | 8/2013 | Gaddam et al. |
| 2013/0197613 | A1 | 8/2013 | Kelly et al. |
| 2013/0223664 | A1 | 8/2013 | Meskens et al. |
| 2013/0238055 | A1 | 9/2013 | Marnfeldt et al. |
| 2013/0268025 | A1 | 10/2013 | Ranu |
| 2013/0278226 | A1 | 10/2013 | Cong et al. |
| 2013/0317584 | A1 | 11/2013 | Stevenson et al. |
| 2014/0058482 | A1 | 2/2014 | Gupta et al. |
| 2014/0070761 | A1 | 3/2014 | Labbe et al. |
| 2014/0155947 | A1 | 6/2014 | Kroll et al. |
| 2014/0247954 | A1 | 9/2014 | Hall et al. |
| 2014/0270211 | A1 | 9/2014 | Solum et al. |
| 2014/0275730 | A1* | 9/2014 | Lievens ............... H04R 25/606 600/25 |
| 2014/0309712 | A1 | 10/2014 | Masaki et al. |
| 2014/0350652 | A1 | 11/2014 | Suwito |
| 2015/0125012 | A1 | 5/2015 | Sabin |
| 2015/0174416 | A1 | 6/2015 | Angara et al. |
| 2015/0224312 | A1 | 8/2015 | Platz et al. |
| 2015/0256945 | A1 | 9/2015 | Mazanec |
| 2015/0374988 | A1 | 12/2015 | Laudanski |
| 2015/0375003 | A1 | 12/2015 | Meskens |
| 2016/0050500 | A1 | 2/2016 | Liao et al. |
| 2016/0227333 | A1 | 8/2016 | Babico |
| 2017/0043162 | A1 | 2/2017 | Lopez-Poveda |
| 2017/0077938 | A1 | 3/2017 | Heubi |
| 2017/0094396 | A1 | 3/2017 | Chandramohan et al. |
| 2017/0161449 | A1 | 6/2017 | Meskens |
| 2017/0259072 | A1 | 9/2017 | Newham et al. |
| 2017/0360364 | A1 | 12/2017 | Heasman et al. |
| 2018/0028811 | A1 | 2/2018 | Van Gerwen et al. |
| 2018/0028827 | A1 | 2/2018 | Schilling et al. |
| 2018/0041848 | A1 | 2/2018 | Nielsen et al. |
| 2018/0050197 | A1 | 2/2018 | Mazanec et al. |
| 2018/0050198 | A1* | 2/2018 | Mazanec ........... A61N 1/36038 |
| 2018/0050203 | A1 | 2/2018 | Mazanec et al. |
| 2018/0059870 | A1 | 3/2018 | Krah |
| 2018/0264269 | A1 | 9/2018 | Meadows |
| 2018/0317027 | A1 | 11/2018 | Bolner et al. |
| 2018/0333577 | A1* | 11/2018 | Nygard ............. A61N 1/36039 |
| 2018/0361151 | A1 | 12/2018 | Ridler et al. |
| 2019/0045308 | A1 | 2/2019 | Chen et al. |
| 2019/0046116 | A1 | 2/2019 | Shah et al. |
| 2019/0190296 | A1 | 6/2019 | Paralikar et al. |
| 2019/0217101 | A1 | 7/2019 | Shi et al. |
| 2019/0231203 | A1 | 8/2019 | Harczos |
| 2019/0344073 | A1 | 11/2019 | Baker et al. |
| 2019/0358450 | A1 | 11/2019 | Lo et al. |
| 2020/0238075 | A1 | 7/2020 | Mazanec et al. |
| 2020/0269034 | A1 | 8/2020 | Mazanec et al. |
| 2020/0269035 | A1 | 8/2020 | Mazanec et al. |
| 2020/0269047 | A1 | 8/2020 | Mazanec et al. |
| 2020/0269048 | A1 | 8/2020 | Mazanec et al. |
| 2020/0269057 | A1 | 8/2020 | Mazanec et al. |
| 2020/0269058 | A1 | 8/2020 | Mazanec et al. |
| 2021/0121707 | A1 | 4/2021 | Fried et al. |
| 2021/0135704 | A1 | 5/2021 | El-Hoiydi et al. |
| 2021/0187293 | A1 | 6/2021 | Friedling |

(56) References Cited

U.S. PATENT DOCUMENTS

| | | |
|---|---|---|
| 2021/0361194 A1 | 11/2021 | Arab et al. |
| 2022/0070594 A1 | 3/2022 | Mazanec |
| 2022/0203104 A1 | 6/2022 | Hernandez et al. |
| 2022/0339445 A1 | 10/2022 | Litvak et al. |

FOREIGN PATENT DOCUMENTS

| | | |
|---|---|---|
| DE | 4419070 A1 | 12/1994 |
| DE | 60107062 T2 | 12/2004 |
| DE | 102013214049 B4 | 3/2015 |
| EP | 1043914 A2 | 10/2000 |
| EP | 1683544 B1 | 11/2010 |
| EP | 2884766 B1 | 2/2018 |
| JP | 2016024111 A | 2/2016 |
| TW | 201142830 A | 12/2011 |
| WO | 2007137032 A2 | 11/2007 |
| WO | 2010056768 A1 | 5/2010 |
| WO | 2014037888 A1 | 3/2014 |
| WO | 2014054215 A1 | 4/2014 |
| WO | 2015077773 A1 | 5/2015 |
| WO | 2016122606 A1 | 8/2016 |
| WO | 2017100866 A1 | 6/2017 |
| WO | 2018035329 A1 | 2/2018 |
| WO | 2018144732 A1 | 8/2018 |
| WO | 2020172500 A1 | 8/2020 |

\* cited by examiner

COMBINATION HEARING AID AND COCHLEAR IMPLANT SYSTEM

RELATED MATTERS

This application is a continuation of U.S. patent application Ser. No. 17/109,304, filed Dec. 2, 2020, the contents of which are incorporated herein by reference.

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

In some cases, external auditory aid devices, such as external hearing aids, can artificially modify sounds prior to their being received by a cochlear implant system. Accordingly, in some such cases, the cochlear implant system receives an artificial representation of sounds in the environment. If the cochlear implant system is programmed to operate without the artificial change by the external auditory aid device, the cochlear implant system may provide an undesirable hearing experience and/or an inaccurate representation of the original acoustic signals to a user.

SUMMARY

Some aspects of the disclosure are generally directed toward cochlear implant systems and methods of operating an implantable cochlear implant that can be used in conjunction with one or more external auditory aid devices, such as an external hearing aid. In some examples, the system may comprise a cochlear implant system. Example cochlear implant systems can include a cochlear electrode, a stimulator, an input source, a signal processor, and an implantable battery and/or communication module. The stimulator may be in electrical communication with the cochlear electrode and the input source may be configured to receive a stimulus and generate an input signal representative of the received stimulus, wherein the received stimulus is representative of an external acoustic signal. Additionally, the implantable battery and/or communication module may be in communication with the signal processor and be configured to provide electrical power to the signal processor. In some embodiments, the cochlear implant system may be configured to receive a status indicator signal indicate of whether an external auditory aid device is active and update the transfer function of the signal processor to compensate for operation of the external auditory aid device is the external auditory aid device is active.

Additionally, the system may further comprise a memory in communication with the signal processor. The memory may include one or more transfer functions, such as a first transfer function and a second transfer function, the first transfer function being different than the second transfer function. Furthermore, updating the transfer function of the signal processor to compensate for the operation of the external auditory aid device if the external auditory aid device is active may comprise changing between transfer functions stored in memory. For instance, in an example, if the external auditory aid device is not active, the signal processor can be programmed with the first transfer function. If the external auditory aid device is active, the signal processor can be programmed with the second transfer function. In some embodiments, the second transfer function is based on operating characteristics of the external auditory device.

In some embodiments, receiving the status indicator signal indicative of whether or not the external auditory aid device is active comprises receiving a first wireless communication indicating whether the external auditory aid device is active. Additionally, the first wireless communication indicating whether the external auditory aid device is active may further comprise information regarding the operation of the external auditory aid device. In some such examples, updating the transfer function of the signal processor to compensate for the operation of the external auditory aid device if the external auditory aid device is active comprises updating the transfer function based on the operation of the external auditory aid device.

In some embodiments, the system may comprise an external hub including a speaker and a wireless communication interface. The external hub may be configured to emit a first acoustic signal via the speaker and communication information regarding the first acoustic signal to the implantable battery and/or communication module via the wireless communication interface. In such embodiments, the implantable battery and/or communication module may be configured to receive information from the external hub regarding the first acoustic signal and receive information from the signal processor from the input source representative of the first acoustic signal and any amplification of the first acoustic signal by the external auditory aid device. Furthermore, the implantable battery and/or communication module may be further configured to analyze the information received from the external hub regarding the first acoustic signal and the information received from the signal processor to determine a relationship between the first acoustic signal from the speaker and the resulting signal generated via the input source and update a transfer function in response to the determined relationship. Such processes can be performed with and without an external auditory aid device active, for example, to update first and second transfer functions.

DETAILED DESCRIPTION

Figure 1:
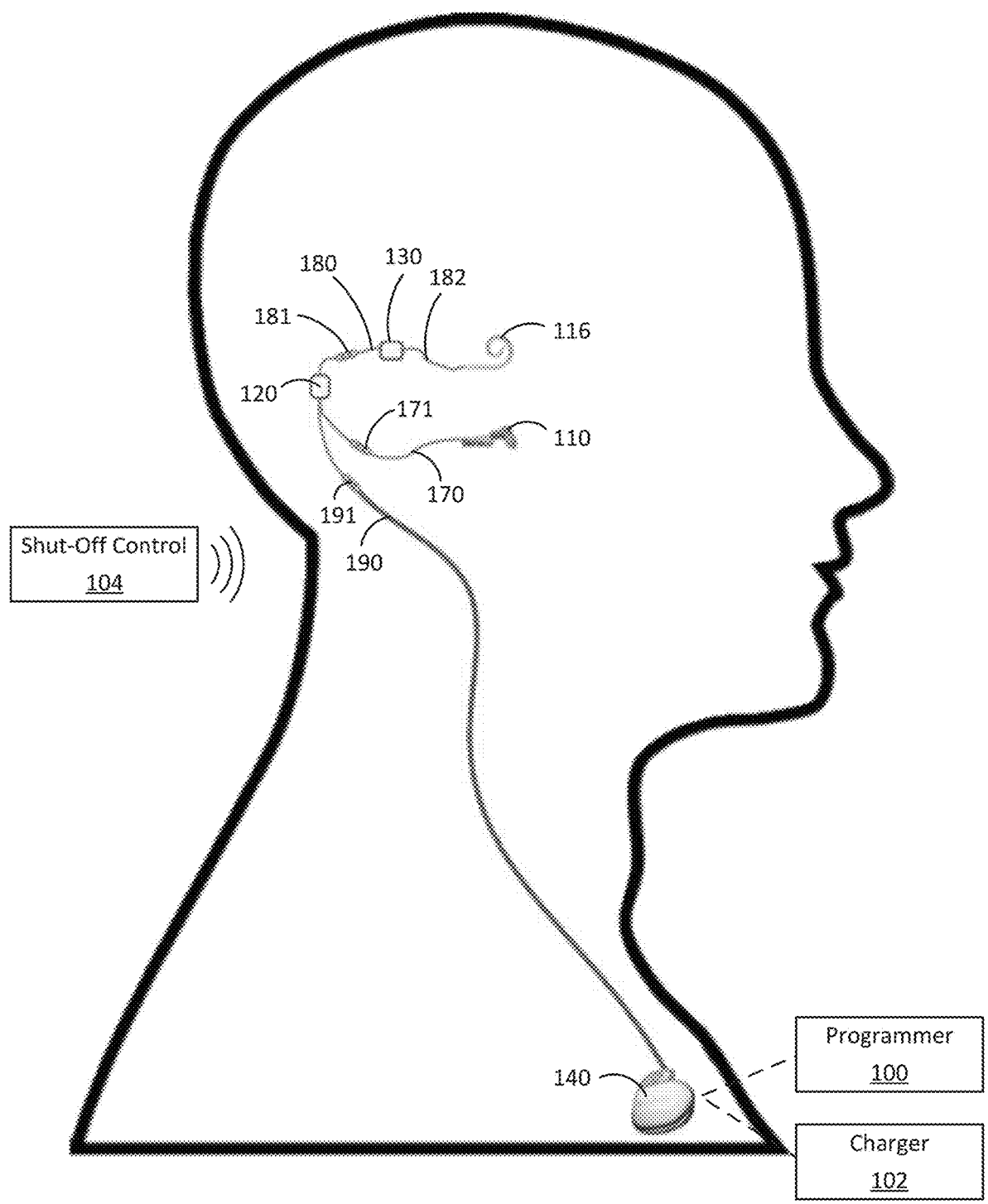
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

In various examples, the signal processor 120 can comprise any variety of components, for example, digital and/or analog processing components. In some embodiments, signal processor 120 comprises a digital signal processor, one or more microprocessors, microcontrollers, application specific integrated circuits (ASICs) or the like. Supporting circuitry for one or more such components can also be included as a part of the signal processor. In some embodiments, the signal processor can include or otherwise communicate with a memory containing programming for operating one or more components. Additionally or alternatively, in some embodiments, the signal processor can include one or more additional components. For example, in some embodiments, signal processor can include an embedded microphone or other sensor configured to detect incoming sound waves.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In the illustrated embodiment, the cochlear electrode 116 is in electrical communication with the electrical stimulator 130 via lead 182. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
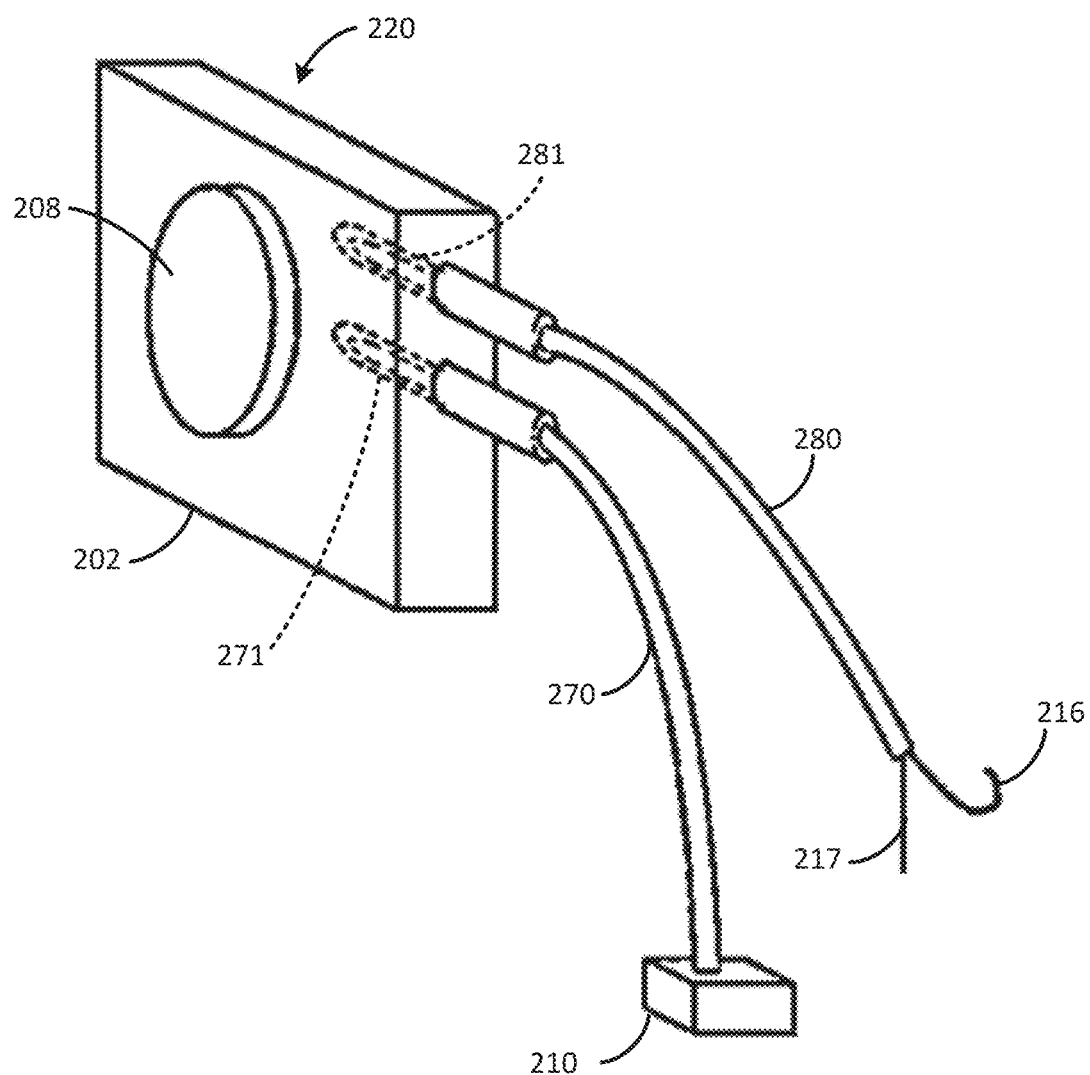
FIG. 2 shows an embodiment of a fully-implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. Such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3:
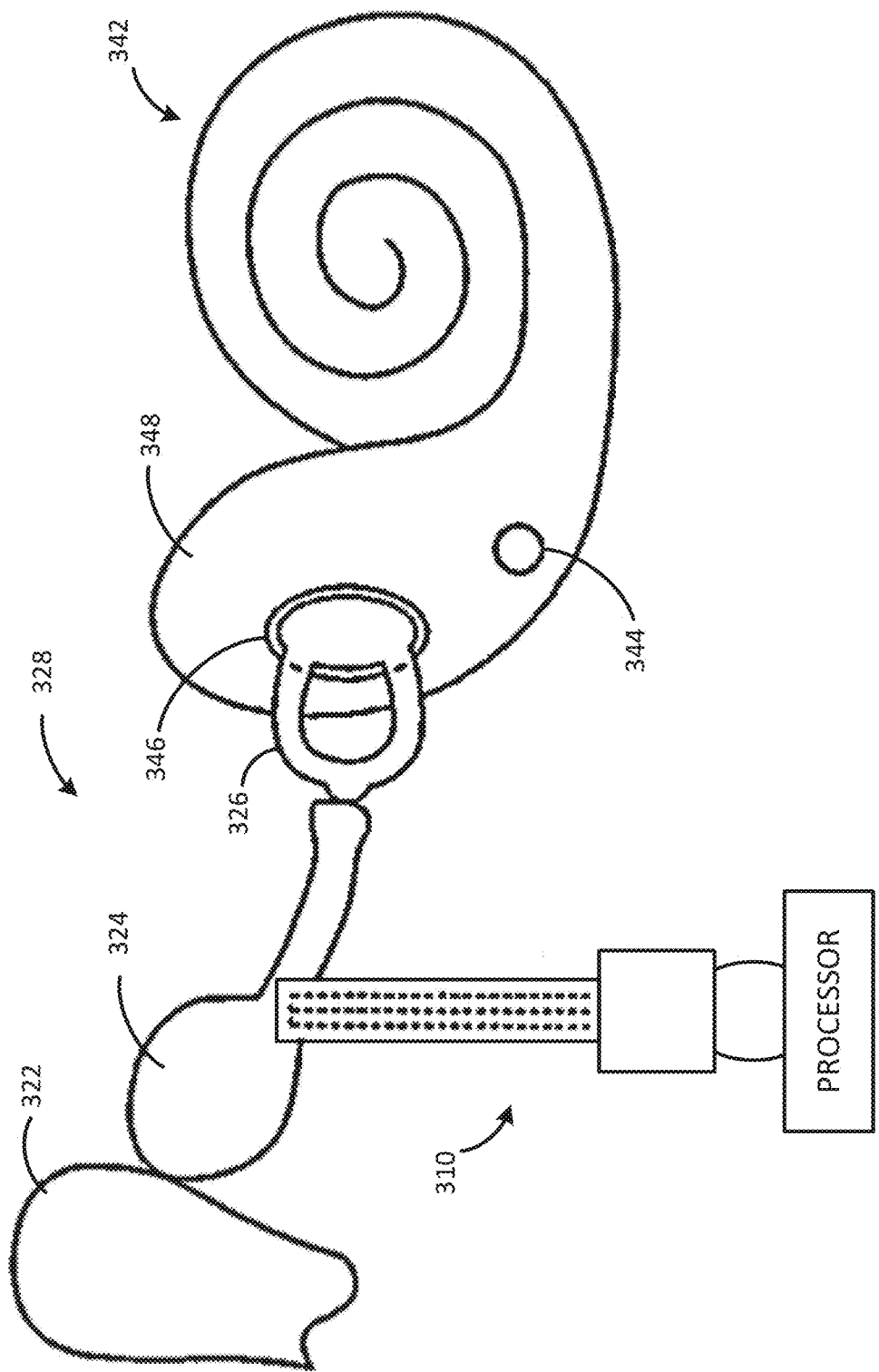
FIG. 3 illustrates an embodiments of an exemplary middle ear sensor for use in conjunction with anatomical features of a patient.

FIG. 3 illustrates embodiments of an exemplary middle ear sensor for use in conjunction with anatomical features of a patient. Referring to FIG. 3, an embodiment of the sensor 310 of a fully-implantable cochlear implant is shown. Also shown are portions of the subject's anatomy, which includes, if the subject is anatomically normal, at least the malleus 322, incus 324, and stapes 326 of the middle ear 328, and the cochlea 348, oval window 346, and round window 344 of the inner ear 342. Here, the sensor 310 is touching the incus 324. The sensor 310 can include a sensor such as described in U.S. Patent Publication No. 2013/0018216, which is incorporated by reference. Further, although not shown in a drawing, the sensor 310 may be in operative contact with the tympanic membrane or the stapes, or any combination of the tympanic membrane, malleus 322, incus 324, or stapes 326.

FIG. 3 illustrates an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function. Additionally or alternatively, systems can include other types of sensors, such as inner ear sensors. Some example configurations of such systems and other sensor arrangements are described in PCT patent application No. PCT/US20/19166, filed Feb. 21, 2020, which is assigned to the assignee of the instant application and is incorporated by reference.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140.

In some embodiments, the implantable battery and/or communication module 140 can communicate with one or more external components, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient. In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. Example detachable connectors are described in PCT patent application No. PCT/US20/19166, which is incorporated by reference. For example, with reference to FIG. 1, in some embodiments, lead 170 can include a first lead extending from the middle ear sensor 110 having one of a male or a female connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120. For example, in an exemplary embodiment, the signal processor 120 can include a female connector integrated into a housing of the signal processor 120. Lead 170 can extend fully from the middle ear sensor 110 and terminate at a corresponding male connector for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery included in the implantable battery and/or communication module 140 may eventually wear out and need replacement. The implantable battery and/or communication module 140 can be replaced or accessed (e.g., for replacing the battery) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a modular signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 4:
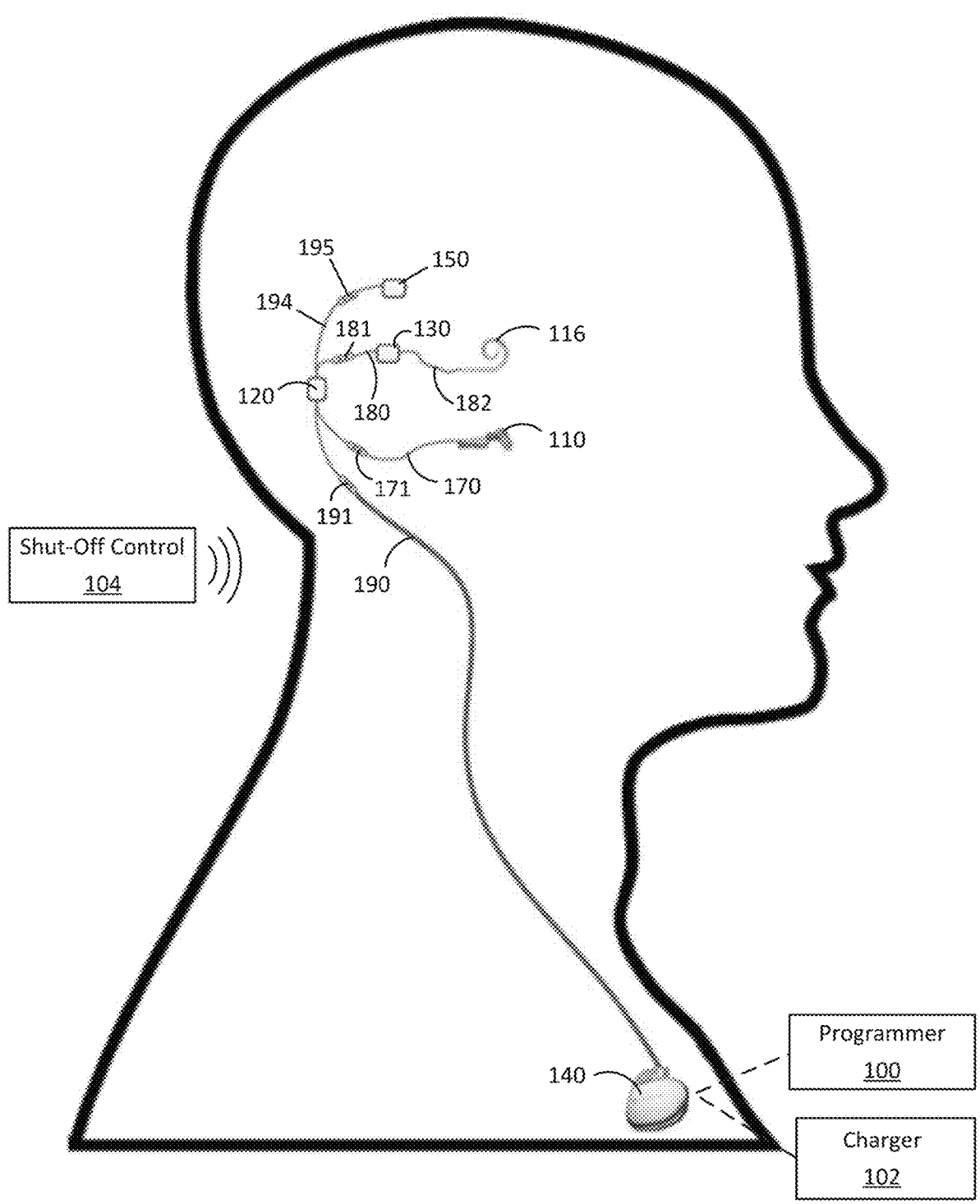
FIG. 4 is a schematic diagram illustrating an exemplary implantable system including an acoustic stimulator.

FIG. 4 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator in in response to input signals from the middle ear sensor according to a transfer function of the signal processor.

The acoustic stimulator of FIG. 4 can be used similarly to the electrical stimulator as described elsewhere herein. For instance, an acoustic stimulator can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

In general, systems incorporating an acoustic stimulator such as shown in FIG. 4 can operate in the same way as systems described elsewhere herein employing an electrical stimulator and cochlear electrode only substituting electrical stimulation for acoustic stimulation. The same modularity benefits, including system maintenance and upgrades.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

With further reference to FIGS. 1 and 4, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

In some examples, implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component). Various systems and methods can be employed provide communication between system components. Some examples of possible communication techniques are described in PCT patent application No. PCT/US20/19166, which is incorporated by reference. In some examples, data can be communicated to the implantable battery and/or communication module from an external component, such as a programmer as shown in FIG. 1. In an exemplary process, a programmer, such as a clinician's computer, can be used to communicate with a patient's fully implanted system via the implantable battery and/or communication module, which can communicate information to other system components, such as via lead 190.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945, entitled TRANSDUCER IMPEDANCE MEASUREMENT FOR HEARING AID, which is assigned to the assignee of the instant application, the relevant portions of which are incorporated by reference herein.

While shown in several embodiments (e.g., FIGS. 1 and 4) as being separate components connected by a lead (e.g., lead 180), in some examples, the processor (e.g., 120) and the stimulator (e.g., 130) can be integrated into a single component, for example, within a hermetically sealed housing, as shown and discussed in PCT patent application No. PCT/US20/19166, which is incorporated by reference.

As described elsewhere herein, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function.

In some situations, a wearer of a cochlear implant system (e.g., a system such as shown in FIG. 1) may additionally use an external auditory aid device, such as an external hearing aid. Such external auditory aid devices may receive and amplify sounds before they reach an input source of an in-use cochlear implant system. However, operating parameters of an external auditory aid device (e.g., gain across a range of frequencies) can change the resulting output of the cochlear implant system if the system is programmed to operate without the presence of the external auditory aid device. This can result in the resulting stimulation being skewed because of the unexpected operation of the external auditory aid device. Such a stimulation may provide an inaccurate and/or uncomfortable hearing experience for the patient, and thus the operation of the of the implantable cochlear implant system may need to be adjusted or temporarily adjusted to compensate for the presence of an active external auditory aid device.

Figure 5A:
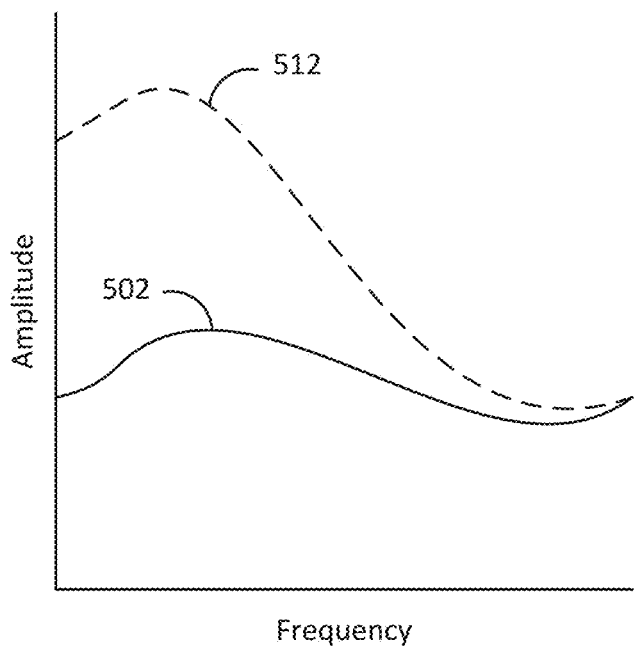
FIGS. 5A and 5B show an illustration demonstrating how an external aid device can affect operation of a cochlear implant system.
Figure 5B:
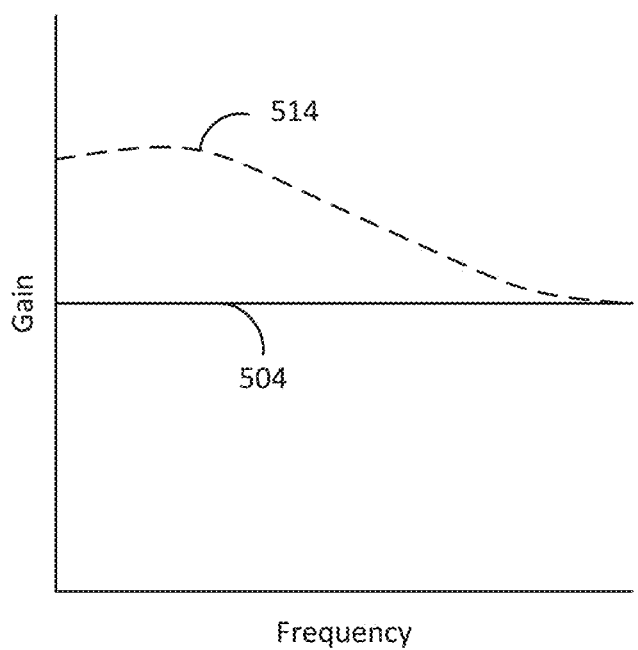

FIGS. 5A and 5B show an illustration demonstrating how an external aid device can affect operation of a cochlear implant system. FIG. 5A shows an example plot of amplitude as a function of frequency output from the cochlear implant system. Solid line 502 shows the amplitude as a function of frequency of the cochlear implant system without an external auditory aid device active. Broken line 512 shows the amplitude as a function of frequency when an external auditory aid device amplifying low frequencies is active. As shown, the signal shape is significantly affected by additional amplification in the low frequencies, which can skew the perception of a sound by the wearer.

FIG. 5B shows an example plot of gain of an overall system (e.g., an external auditory aid device and cochlear implant system) as a function of frequency. Similar to FIG. 5A, solid line 504 shows gain of a cochlear implant system across a range of frequencies when no external auditory aid device is active. As shown, the gain is flat or approximately flat across the range of frequencies. Various benefits of and ways of achieving such an approximately flat gain curve are described in PCT patent application No. PCT/US20/19166, which is incorporated by reference. Broken line 514 shows an effective gain curve of the system when an external auditory aid device amplifying low frequencies is active. As shown, the gain is no longer flat across the range of frequencies due to the operation of the external auditory aid device. As noted above, this can skew the perception of a sound by a wearer. While FIGS. 5A and 5B show an example in which an external auditory aid device amplifies lower frequencies more than higher frequencies, similar concepts may apply for any amplification provided by the external auditory aid device, such as if the device amplifies higher frequencies or the like. In some cases, any unexpected manipulation of sounds by an external auditory aid device prior to the sound reaching an input source of the cochlear implant system can result in the cochlear implant system operating undesirably.

Figure 6:
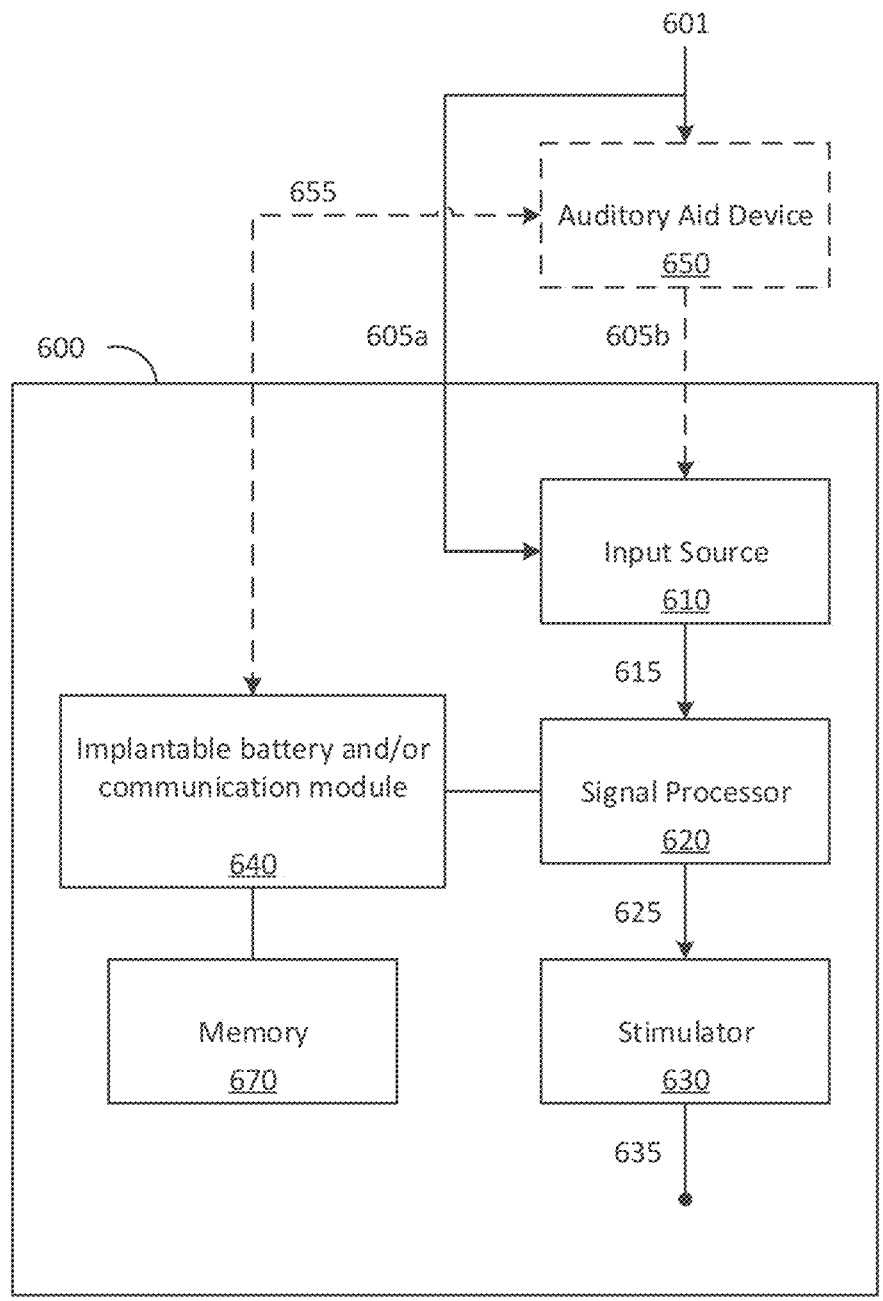
FIG. 6 provides an exemplary flow chart illustrating how an external stimulus may be received, processed, and then provided to a cochlear electrode.

In some embodiments, a cochlear implant system can be configured to compensate for operation of an external auditory aid device in order to reduce or eliminate the skewing of perceived sounds like those illustrated by the examples in FIGS. 5A and 5B. FIG. 6 provides an schematic diagram illustrating example operation of an external auditory device with a cochlear implant system. As shown, an input source 610 of a fully-implantable cochlear implant system 600 may be configured to receive a stimulus 605a from an external stimulus 601. As similarly discussed herein, the input source 610 may generate an input signal 615 based on the received stimulus 605a and output the input signal 615 to a signal processor 620. The signal processor 620 may receive the input signal 615 and output a stimulation signal 625 to a stimulator 630. In some embodiments, the signal processor 620 may be programmed with one or more transfer functions and is configured to receive one or more input signals 615 from the input source 610 and output the stimulation signal 625 to the stimulator 630 based on the received one or more input signals 615 and one or more other the transfer functions. Furthermore, the stimulator 630 may be configured to receive the stimulation signal 625 and generate a signal 635 to provide to a cochlear electrode, an acoustic stimulator, or the like.

As discussed herein, the fully-implantable cochlear implant system 600 may additionally comprise an implantable battery and/or communication module 640. The implantable battery and/or communication module 640 may be in communication with the signal processor 620 and may be configured to provide electrical power to the signal processor 620. Additionally or alternatively, the fully-implantable cochlear implant system may comprise a memory 670 in communication with the signal processor 620. In some embodiments, such as shown in FIG. 6, the memory 670 may be in communication with the signal processor via implantable battery and/or communication module 640. However, memory 670 may be additionally or alternatively in direct communication with the signal processor 620.

In some embodiments, additional devices, such as external auditory aid device 650, may be used to provide auditory aid to a patient. External auditory aid device 650 may comprise a variety of devices, such as an external hearing aid or other audio amplifier and/or filter that changes one or more characteristics of acoustic signal prior to its being received by an input source of the cochlear implant system (e.g., prior to entering the ear canal and being detected via a middle ear sensor). External auditory aid device 650 can be configured to receive an external stimulus 601 and output a modified stimulus 605b based on the properties of the external auditory aid device 650. For example, in embodiments wherein the external auditory aid device 650 comprises an external hearing aid, the external auditory aid device 650 may be configured to receive the external stimulus 601 and artificially modify the external stimulus 601, such as by amplifying lower frequency sounds as shown in the examples of FIGS. 5A and 5B.

As discussed herein, because of the operation of the external auditory aid device 650, stimulus 605b may be significantly different from stimulus 605a. As such, various issues may arise as the signal is transferred through various components of the fully-implantable cochlear implant system. Processing a stimulus 605b resulting from operation of external auditory aid device 650 rather than stimulus 605a may provide an inaccurate representation of the external stimulus 601 to a patient if the cochlear implant system 600 operates as if external auditory aid device 650 was not present or active.

In some examples, the cochlear implant system 600 can be configured to communicate with the external auditory aid device 650 via a wireless communication link 655. For instance, in some embodiments, the external auditory aid device 650 can communicate wirelessly with the implantable battery and/or communication module 640 of cochlear implant system 600 such as shown in the example of FIG. 6. In some examples, the cochlear implant system 600 can determine if or when the external auditory aid device 650 is active based on information received via wireless communication link 655.

Additionally, in some examples, to reduce or eliminate any inaccurate representations of the external stimulus 601, the transfer function used by the signal processor 620 may be updated or adjusted based on whether the external auditory aid device 650 is active. For example, the fully-implantable cochlear implant system 600 may be configured to receive information regarding whether the external auditory aid device is active. In some examples, cochlear implant system 600 can receive a status indicator signal via wireless communication link 655 indicative of operation of an external auditory aid device (e.g., whether the external auditory aid device is active). In some such embodiments, the presence of a status indicator signal received via wireless communication link 655 may indicate that the external auditory aid device 650 is active and the absence of such a status indicator signal via wireless communication link 655 may indicate that the external auditory aid device 650 is inactive.

In some embodiments, a status indicator signal may be communicated directly from external auditory aid device 650 to the cochlear implant system 600 via wireless communication link 655. Additionally or alternatively, in some embodiments, such status indicator signal may be received by the cochlear implant system 600 from other sources, such as an external control device (e.g. computer, tablet, phone, wearable device, programmer, fob, or the like).

Additionally or alternatively, the status indicator signal may be manually sent by a user, such as a wearer of the cochlear implant system (e.g. via an external control device). In some such instances, the user may provide a status indicator signal indicating whether the external auditory aid device is active, one or more operating parameters of the external auditory aid device, or the like. In some examples, a user may send a status indicator signal upon turning on the external auditory aid device, turning off the external auditory aid device, changing the settings on the external auditory aid device, or the like. In the various embodiments, a status indicator signal may be received over wireless communication, such as via NFC, Bluetooth, or the like.

In some embodiments, the status indicator signal may comprise an initial signal, such as a signal representing a change in the external auditory aid device (e.g. changing to active, changing to inactive, a different adjustment, or the like). Additionally or alternatively, the status indicator signal may comprise a continuous or intermittent signal, such as a signal representing the current state of the external auditory aid device. In some embodiments, the implantable cochlear implant system may additionally communicate with the external auditory aid device 650 (directly and/or indirectly via an external control device), such as to request information from the external auditory aid device, provide diagnostic information, or the like.

In some examples, once a status indicator signal is received indicating that the external auditory aid device is active, the transfer function of the signal processor 620 may be updated to compensate for the operation of the external auditory aid device 650. As discussed herein, updating the transfer function to compensate for the operation of the external auditory aid device 650 may help reduce or eliminate skewing of the signal such as illustrated in FIGS. 5A and 5B.

Figure 7:
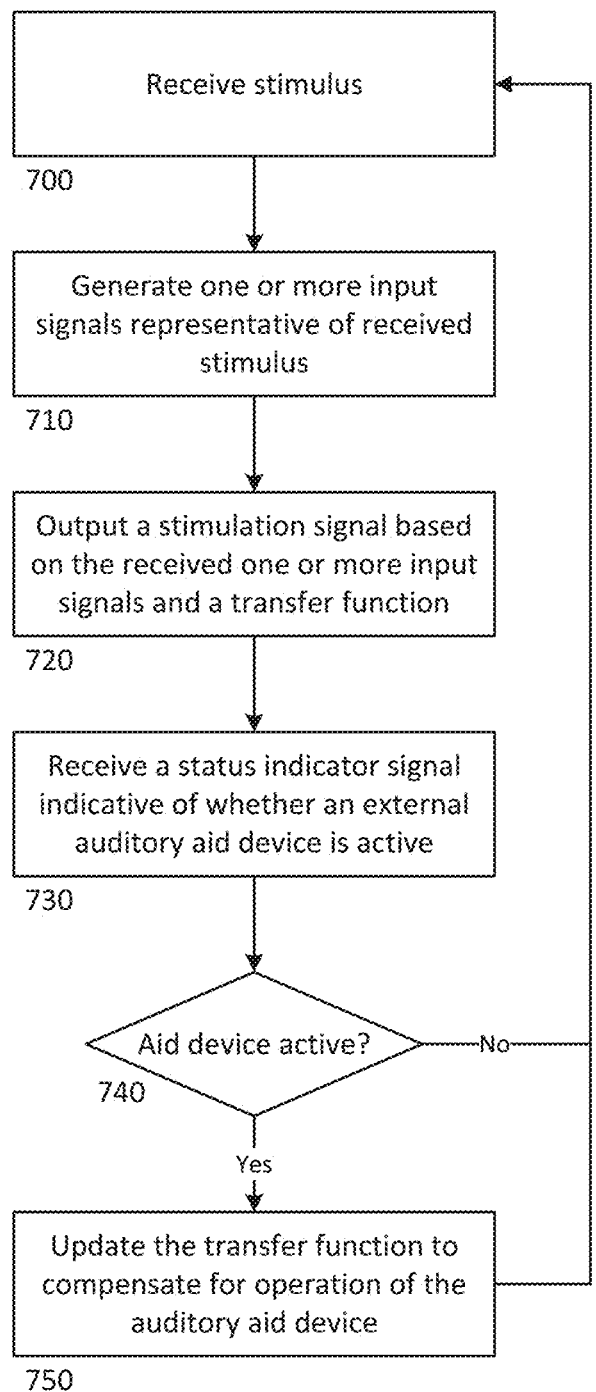
FIG. 7 provides an exemplary method of updating a transfer function to compensate for the operation of an external auditory aid device.

FIG. 7 provides an exemplary method of updating a transfer function to compensate for the operation of an external auditory aid device (e.g. external auditory aid device 650). As shown in step 700, a stimulus (e.g. stimulus 605a, stimulus 605b, or the like) may be received by the cochlear implant system (e.g. fully-implantable cochlear implant system 600), such as by an input source (e.g. input source 610). The cochlear implant system can generate one or more input signals (e.g. input signal 615) based on the received stimulus (710) and output a stimulation signal (e.g. stimulation signal 625) based on the received input signal(s) and a transfer function (720).

In some embodiments, as shown in step 730, the method may further comprise receiving a status indicator signal (e.g. via wireless communication interface 655) indicative of whether an external auditory aid device (e.g. external auditory aid device 650) is active. If an external auditory aid device is not active ("No" in step 740), the system can continue to operate in the same manner with the same transfer function. However, if an aid device (e.g. external auditory aid device 650) is active (e.g. "Yes" in step 740), the method includes updating the transfer function to compensate for the operation of the external auditory aid device (750). For example, the cochlear implant system can be configured to adjust the transfer function based on a gain profile of the external auditory aid device, such as by adjusting the transfer function to reduce gain in low frequencies if the external auditory aid device has higher gain in low frequencies.

In various embodiments, updating the transfer function as shown in step 750 of FIG. 7 can be performed in a variety of ways. For instance, in some embodiments, the signal processor 620 may be configured to use a first transfer function when the external auditory aid device 650 is inactive (e.g. the input source 610 receives stimulus 605a) and use a second transfer function when the external auditory aid device 650 is active (e.g. the input source 610 receives stimulus 605b). Furthermore, the first transfer function may be different than the second transfer function, for example, to compensate for the differences between stimulus 605a and stimulus 605b received at an input source. In some examples, such transfer functions can be stored in memory (e.g., 670 in FIG. 6) such that the transfer functions can be implemented based on whether the external auditory aid device is active.

In such embodiments, the transfer function used in step 720 may be dependent on a received status indicator signal indicating one or more operating parameters of the external auditory aid device. For instance, in some examples, the cochlear implant system can be configured to determine one or more operating characteristics based on the status indicator signal received from an external auditory aid device and update the transfer function in response thereto. In an example embodiment, the status indicator signal can include information about gain vs. frequency of the external auditory aid device, and the system can be configured to update the transfer function to accommodate such a gain profile. For instance, in an example embodiment, the system can be configured to update the transfer function so that, when coupled with the operating characteristics of the external auditory aid device, the transfer function provides a desired gain response across a given frequency range (e.g., an approximately flat gain curve across a range of frequencies).

In various examples, updating the transfer function can include modifying one or more aspects of an existing transfer function or creating and implementing a new transfer function in view of the operating parameters of the external auditory aid device.

However, in some embodiments, one or more of the transfer functions may initially be not calibrated or created for optimized use with an external auditory aid device once the external auditory aid device becomes active (or updated to use updated operating parameters). For example, a cochlear implant system (e.g. fully-implantable cochlear implant system 600) may lack information (e.g. stored in memory 670 or the like) regarding a specific transfer function for use when the external auditory aid device 650 is active. Additionally or alternatively, the settings of the external auditory aid device 650 and/or the cochlear implant system may be adjusted to the point that a transfer function for use when the external auditory aid device is active should be updated to reflect such changes. For example, a second transfer function stored in memory for use when an external auditory aid device may be suitable in some cases, but be less so in the event that operating parameters of the external auditory aid device are changed. Accordingly, in some examples, cochlear implant systems can be configured to establish or update transfer functions to be used to compensate for operation of an external auditory aid device.

In some cases, because of the nature of relationship between incoming external acoustic source and the stimulation received by a patients cochlea, adjusting the operation of the implantable cochlear system to compensate for the presence of an active external auditory aid device may comprise a more complicated relationship than simply raising or lowering the gain in the implantable cochlear implant system. For example, the external auditory aid device may use one or more gain control loops including one or more time constants other characteristics to adjust received external acoustic signals. Such operating parameters of the external auditory aid device could skew the acoustic signals provided to an input source of the cochlear implant system and accordingly provide a wearer with an inaccurate representation of the external acoustic signal.

In some embodiments, a status indicator signal can include operating characteristics of the external auditory aid device, such as gain profiles, time constants, control loop values, or the like associated with the operation of the external auditory aid device. In some such examples, a cochlear implant system can be configured to update the transfer function of the signal processor to accommodate for the operating characteristics of the external auditory aid device.

For example, in some embodiments, the signal processor of the cochlear implant system includes front end automatic gain control (AGC) including a non-linear gain control, for example, where soft sounds are amplified more than loud sounds. Such gain control can include time-based characteristics (e.g., one or more time constants associated with the gain control), for example, how quickly the gain changes over time, and such time-based characteristics can be important for understanding various sounds, such as speech. Suboptimal time-based characteristics in a gain control step can therefore negatively impact speech or other sound recognition.

External auditory aid devices often include similar AGC functions with time-based characteristics. However, when an external auditory aid device and cochlear implant system operate together, gain control features of each component may combine to ultimately skew time-based characteristics of the overall acoustic processing. Additionally, non-linear gain applied in both the external auditory aid device and the cochlear implant system can further skew the overall gain and yield undesirable results.

Accordingly in some examples, a cochlear implant system can be configured to update an internal AGC function in response to a received status indicator signal indicating the presence and operation of an external auditory aid device. For instance, in some examples, the status indicator signal includes information regarding one or more AGC parameters of the external auditory aid device (e.g., one or more time-based characteristics). The cochlear implant system can be configured to modify its AGC function in response to the received status indicator signal such that its AGC function and that of the external auditory aid device do not undesirably skew the combined audio processing of the external auditory aid device and the cochlear implant system. In some examples, the cochlear implant system is configured to disable its AGC function in response to a status indicator signal indicating an external auditory aid device is active. In such examples, the combined external auditory aid device and cochlear implant system can utilize the AGC function of the external auditory aid device.

Additionally or alternatively, in some examples, the cochlear implant system can communicate with the external auditory aid device in response to receiving the status indicator signal indicating the presence of an active auditory aid device. In some such examples, the cochlear implant system can instruct the auditory aid device to disable its AGC function while continuing to operate the cochlear implant system with its AGC function. In such examples, the combined external auditory aid device and cochlear implant system can utilize the AGC function of the cochlear implant system.

In some embodiments, the cochlear implant system can be configured to update its transfer function in response to a received status indicator signal regardless of whether it changes or disables its AGC function. Similarly, in some embodiments, the cochlear implant system can be configured to update its transfer function in response to a received status indicator signal regardless of whether the external auditory aid device changes or disables its own AGC function. For example, in some embodiments, a single AGC function (either of the cochlear implant system or of the external auditory aid device) provides the overall AGC function, and the cochlear implant system is configured to update a signal processor transfer function independent of the AGC function in response to the status indicator signal signaling operation of and external auditory aid device.

In some examples, an implantable cochlear implant system may comprise a plurality of operating profiles (e.g., each being associated with a corresponding signal processor transfer function). For instance, in some embodiments, a cochlear implant system can include an operating profile for use when no external auditory aid device is active (e.g., device is inactive and/or not present) and another operating profile for an active external auditory aid device. In some examples, a cochlear implant system can be configured to update an operating profile based on received information regarding the operating characteristics of the external auditory aid device.

Figure 8:
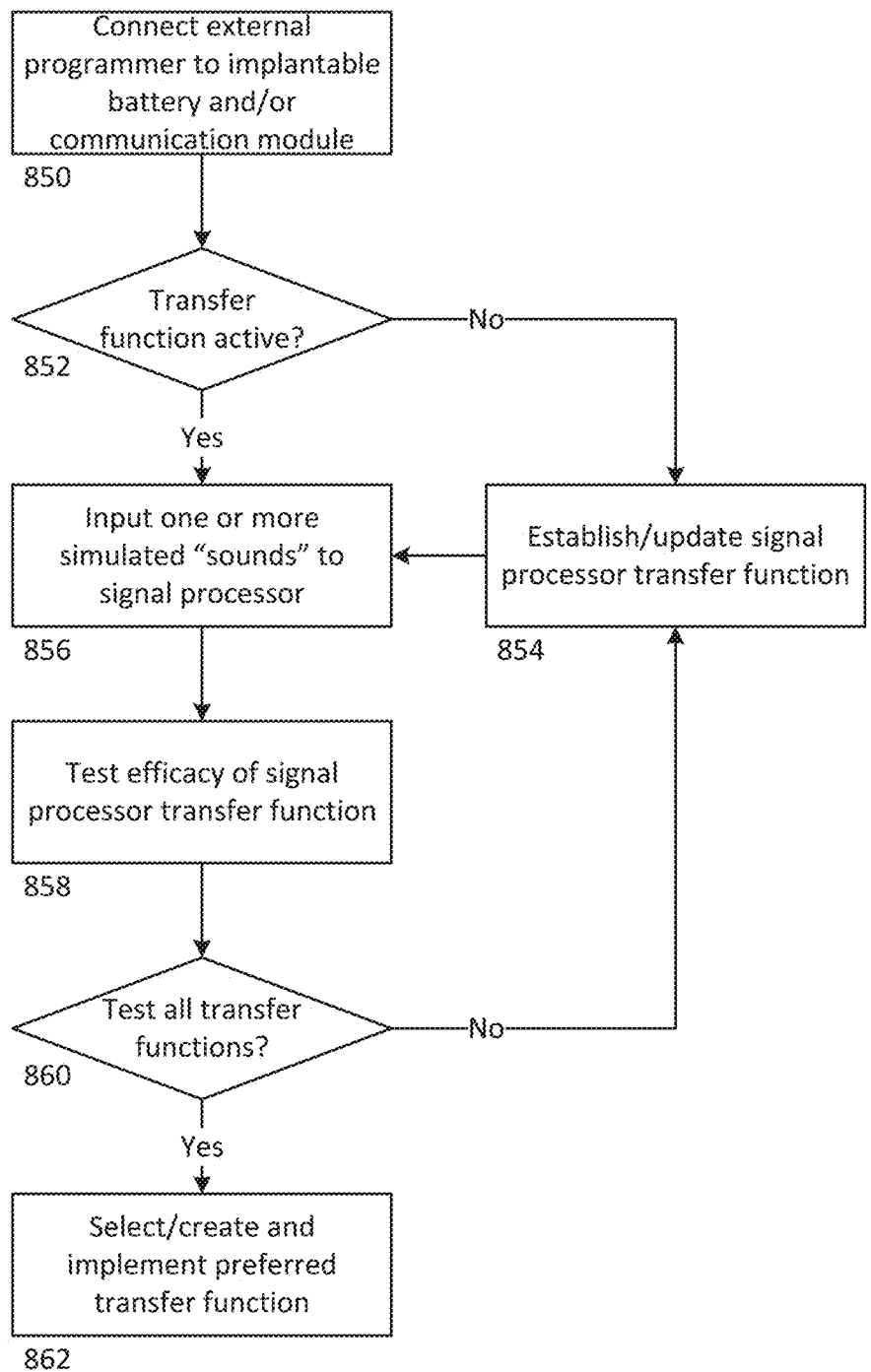
FIG. 8 is a process flow diagram illustrating an exemplary process for establishing a preferred transfer function for a patient.

For instance, in an example embodiment, a cochlear implant system can include at least a first operating profile having a first associated transfer function and a second operating profile having a second associated transfer function. The first operating profile can be used when the system detects no active external auditory aid devices, and the second operating profile can be used when the system detects an active external auditory aid device. The cochlear implant system can be configured to receive information from an external auditory aid device regarding one or more operating characteristics of the external auditory aid device, and the second operating profile (e.g., the second transfer function) can be based the one or more operating characteristics of the auditory aid device FIG. 8 is a process flow diagram illustrating an exemplary process for establishing a preferred transfer function for a patient such as a preferred transfer function for a cochlear implant system comprising an external auditory aid device (e.g. external auditory aid device 650). The method can include connecting an external programmer to the implantable battery and/or communication module (step 850). Connecting can include, for example, establishing a wireless connection (e.g., Bluetooth communication) between an external programmer and the implantable battery and/or communication module. The external programmer can include any variety of components capable of providing programming instructions to the implantable battery and/or communication module, such as a computer, smartphone, tablet, or the like.

Once communication is established, if there is no transfer function active (step 852), a transfer function can be established (step 854). In some embodiments, the check to see if a transfer function is active (step 852) may comprise checking to see if a transfer function is active for present configuration of the cochlear implant system and external auditory aid device. For example, if the settings of the external auditory aid device have been adjusted, a new external auditory aid device is being used, or the like a transfer function may be established or updated (step 854). In such examples, the settings for the external auditory aid device may be used to update the corresponding transfer function prior to testing the efficacy of said transfer function. For example, if the settings of the external auditory aid device were adjusted to provide more or less amplification to lower frequencies, the corresponding transfer function may be updated to reflect the settings of the external auditory aid device, such as by adjusting the lower frequencies of the transfer function accordingly.

If a transfer function is already active, or after one has been established (step 854), the programmer can be used to input one or more simulated "sounds" to the signal processor. Such "sounds" can be received and treated by the signal processor as if they were received from an input source such as a middle ear sensor. The "sounds" can be, for example, computer-generated signals designed to simulate various input signals, such as a range of frequencies, phonetic sounds, or other distinguishable sound characteristics.

The process can further include testing the efficacy of one or more transfer functions (step 858). This can include, for example, determining how well the patient responds to each sound provided a given transfer function. In some examples, this can include rating the transfer function under test for each of the "sounds" and determining an aggregate score for the transfer function based on the score(s) associated with the one or more "sounds."

After testing the efficacy of the transfer function, if not all desired transfer functions have been tested (step 860), the signal transfer function can be updated (step 854). The one or more simulated "sounds" can be input to the signal processor (step 856) and processed according to the updated transfer function, and the efficacy of the updated transfer function can be tested (step 858). Once all desired transfer functions have been tested (step 860), a transfer function for the user can be created or selected and implemented for the patient (step 862). In some examples, a best transfer function of the tested transfer functions is selected based on a user preference, a highest score, or other metric. In other examples, composite results from the tested transfer functions can be combined to create a customized transfer function for the patient. Furthermore, in some embodiments multiple transfer functions may be saved, such as one transfer function for when an external auditory aid device is active and another transfer function for when an external auditory aid device is inactive.

In other examples, rather than continually updating the transfer function, simulated "sounds" can be pre-processed outside of the signal processor, for example, on site with a clinician or audiologist. For instance, in an exemplary process, one or more simulated sounds can be pre-processed using processing software to establish simulated stimulation signals that would result from a particular input signal being processed via a particular transfer function. In some examples, such signals can be transferred to, for example, the signal processor for directly applying stimulation signals to the wearer.

Communication to the stimulator can be performed, for example, directly from various system components, such as a programmer. In other examples, such communication can be performed via the implantable battery and/or communication module and signal processor. For instance, in an exemplary embodiment, pre-processed signals can be communicated to the implantable battery and/or communication module via a wireless (e.g., Bluetooth) communication. The implantable battery and/or communication module can communicate the pre-processed signals to the signal processor, which can be configured with a unity transfer function. Thus, the signal processor merely passes the pre-processed signals on to the stimulator for performing stimulation.

In some embodiments, the one or more "sounds" within the process performed in FIG. 8 can include one or more simulated sounds that are a predicted output from an active external auditory aid device. For example, one or more operating parameters of an external auditory aid device can be used to generate one or more simulated "sounds" to mimic operation of the external auditory aid device. In an example process, the method of FIG. 8 can be performed for a first plurality of simulated "sounds" to create a first transfer function. The process can be repeated for a second plurality of simulated "sounds," the second plurality of simulated "sounds" corresponding to each of the first plurality of simulated "sounds" as would be modified by an external auditory aid device operating with certain operating parameters. The second plurality of simulated "sounds" can be used to establish a second transfer function for use when an external auditory aid device operating with such operating parameters is active (e.g., as determined via a received status indicator signal). In various examples, such a process can be repeated for any number of different external auditory aid device operating parameters to establish a corresponding transfer function for use when the external auditory aid device is active with such operating parameters.

In some embodiments, one or more implanted system components comprises a near field communication component configured to facilitate communication between the system and an external device only when brought into very close proximity to the near field communication component. In some such examples, once near-field communication is established, the pairing for longer-range wireless communication (e.g., Bluetooth) can be established. For instance, in an exemplary embodiment, a charger and an implantable battery and/or communication module can each include near field communication components for establishing a secure, near field communication and subsequently pairing to each other for additional wireless communication.

Figure 9:
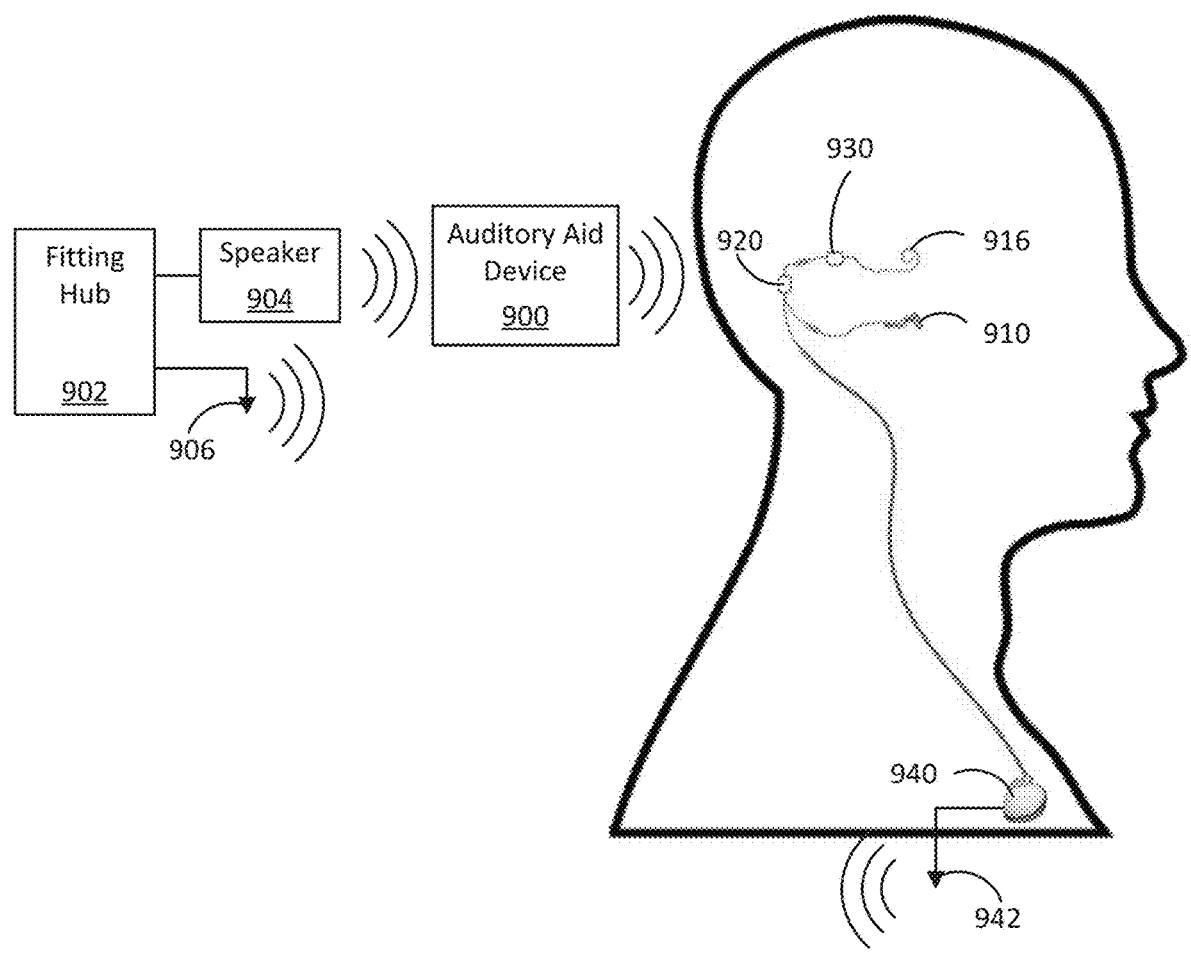
FIG. 9 shows an example configuration of an interfacing device configured to assist in system calibration.

In some embodiments, systems can communicate with external devices to assist in fitting and/or calibrating the implanted system. FIG. 9 shows an example configuration of an interfacing device configured to assist in system calibration. As shown, a fitting hub 902 may be configured to communicate with an external auditory aid device 900 and/or an implantable cochlear implant system. In some embodiments, the fitting hub may comprise or be in communication with a laptop, PC, smartphone, tablet, smartwatch or the like. Additionally or alternatively, the fitting hub 902 may be a standalone device. As shown, the fitting hub 902 may include or otherwise communicate with a speaker 904, which can output a sound based on a command from the fitting hub 902.

In the illustrated example, fitting hub 902 includes a wireless communication interface 906 (e.g., a Bluetooth interface) that can communicate with a communication interface 942 of an implantable battery and/or communication module 940. In some examples, the fitting hub 902 includes or is otherwise capable of interfacing with a near field communication component (e.g., a communication coil) to enable Bluetooth communication between the fitting hub 902 and an implanted system (e.g., via an implantable battery and/or communication module 940) such as described elsewhere herein. Additionally or alternatively, another device (e.g., a charger) can be used to enable wireless (e.g. Bluetooth) communication between the fitting hub 902 and the implantable battery and/or communication module 940.

During an exemplary calibration process, the fitting hub 902 can be configured to output a sound via speaker 904 and also communicate information about the sound (e.g., intensity, frequency content, etc.) to the implantable battery and/or communication module 940 of the implanted system. The implanted system, e.g., via the signal processor 920, can be configured to compare the output of the sensor 910 (received at the signal processor 920) to the actual sound emitted from the speaker 904. This data can be repeated for a plurality of sounds from output from the speaker (e.g., various frequencies and/or amplitudes) and used to determine the relationships between sounds picked up from the sensor 910 and the output from the sensor 910 to the signal processor 920. Based on this information, the signal processor 920 transfer function can be calibrated so that stimulation signals sent to the stimulator 930 based on the output from the sensor 910 accurately represent the sound from the environment. Additionally or alternatively, the information can be used to identify how effectively the sensor responds to various external acoustic stimuli, such as different frequencies, intensities, etc. This information can be determined specifically for the wearer, since the sensor response may depend on various factors specific to the wearer and/or the positioning of the sensor.

In some embodiments, the fitting hub 902 may be configured to output one or more sounds comprising a single frequency and/or single intensity. For example, it may be beneficial to output multiple sounds over the common human hearing range (e.g. 20 to 20,000 Hz). However, other frequency ranges may be used, such as depending on the age of the patient, the hearing abilities of the patient, or the like. In some embodiments, each sound may have a signal frequency component at an intensity, such as various tones. Additionally or alternatively, the one or more sounds may comprise complex frequency and intensity components, such as sounds representing various beeps, words, noises, or other sounds known to one of ordinary skill in the art.

While described as taking place in the implantable system (e.g., the signal processor 920), the calibration process can be similarly performed via the fitting hub 902. For example, the speaker 904 can output a sound based on instructions from the fitting hub 902. The sensor 910 can output a signal based on the sensor response to the sound emitted from the speaker 904, and the signal processor 920 can receive the signal from the sensor 910 and output stimulation signals to the stimulator 930 based on the received signals and the transfer function. In some embodiments, the transfer function may be based on a received status indicator signal, as discussed herein.

In various examples, the implantable battery and/or communication module 940 can be configured to receive any combination of signals from the sensor 910, the stimulation signals from the signal processor 920, or signals representative of one or both of such signals. The implantable battery and/or communication module 940 can then communicate one or more signals to the fitting hub 902 representative of the output of the sensor 910 and/or the signal processor 920 in response to the sound output from speaker 904. The comparison of the sound output from the speaker 904 and the corresponding resulting signal(s) in the implanted system can be performed via processing in the fitting hub 902. Similar to discussed above, this comparison can be used to determine the relationships between sounds picked up from the sensor 910 and the output from the sensor 910 to the signal processor 920. Based on this information, the transfer function can be calibrated so that stimulation signals sent to the stimulator 930 based on the output from the sensor 910 accurately represent the sound from the environment. Additionally or alternatively, the information can be used to identify how effectively the sensor responds to various external acoustic stimuli, such as different frequencies, intensities, etc. This information can be determined specifically for the wearer, since the sensor response may depend on various factors specific to the wearer, the positioning of the sensor, and/or any external auditory aid devices being used.

In some examples, the fitting hub 902 may comprise a user interface in the form of an application on the fitting hub or in communication with the fitting hub. In such embodiments, features and/or functions of the fitting hub 902 can be performed via the application. In some such embodiments, a wearer and/or physician can provide an input via the application, for example, during various processes described herein. In some embodiments, a wearer can receive a sound from the fitting hub 902 and provide input, via the application, indicating whether the sound was heard or not heard, was too loud or too quiet, was distinguishable or not distinguishable from a previous sound, and/or other inputs.

In some examples, an implant system (e.g., via fitting hub 902 or implantable battery and/or communication module 940) can be configured to update a transfer function in response to such received inputs.

In some embodiments, the fitting hub 902 may be configured to communicate to a remote facility, for example, with a physician such as an audiologist. In some such embodiments, the fitting hub 902 includes a remote communication device configured to communicate with such a remote facility, for example, via the internet. The remote communication device configured to communicate with such a remote facility, for example, via the internet. The remote communication device can communicate various information associated with the fitting hub 902, the external auditory aid device 900, and/or the implanted cochlear implants, to an additional device, such as a device used by an audiologist. Additionally or alternatively, the remote communication device can be configured to receive inputs from the remote facility, such as inputs related to features and/or functions performed by the fitting hub, the external auditory aid device, and/or the implanted cochlear implants. For example, in some instances, an audiologist operating at a remote facility can trigger the fitting hub 902 to output one or more predetermined sounds and/or perform one or more fitting functions. Additionally or alternatively, the audiologist can receive information such as the wearers use of the cochlear implant system, the wearers use of the external auditory aid device, update features of one or more devices, receive updates on tests, initiate/run tests, receive any feedback regarding the use or usability of the implantable cochlear implants, and/or the like.

In embodiments comprising an external auditory aid device (e.g. external auditory aid device 900), calibration processes such as discussed herein may be similarly performed to accommodate for situations in which external auditory aid device is active as well as when the external auditory aid device is inactive. In such situations, such exemplary calibration processes can be performed while the external auditory aid device 900 is active such that the transfer function (e.g. a second transfer function) can be calibrated to represent sounds from the environment.

In such a calibration processes, the implanted system can be configured to receive a status indicator signal indicative of whether the external auditory aid device is active. The cochlear implant system can implement a transfer function based on the received status indicator signal (e.g., a first transfer function if the external auditory aid device is inactive and a second transfer function if the external auditory aid device is active.

For instance, with reference to FIG. 6, stimulus 605a (e.g. without any modifications from an external auditory aid device) can include a sound emitted from speaker 904 in FIG. 9, and stimulus 605b may be representative the actual sound emitted from speaker 904 after modifications from an active external auditory aid device 900. Calibration processes such as described herein can comprise determining a relationship between the actual sound (e.g. stimulus 605a) and the resulting signal generated via the input source (e.g. stimulus 605b) (e.g., determining a gain factor associated with the operation of the external auditory aid device). Such a gain factor may be used to update the corresponding transfer function, as described herein.

As described herein, some embodiments may comprise multiple external auditory aid device configurations and/or multiple settings on an auditory aid device. In such embodiments, a calibration process can be performed multiple times, such as for one or more external auditory aid device configurations and/or one or more settings on an external auditory aid device.

Figure 10:
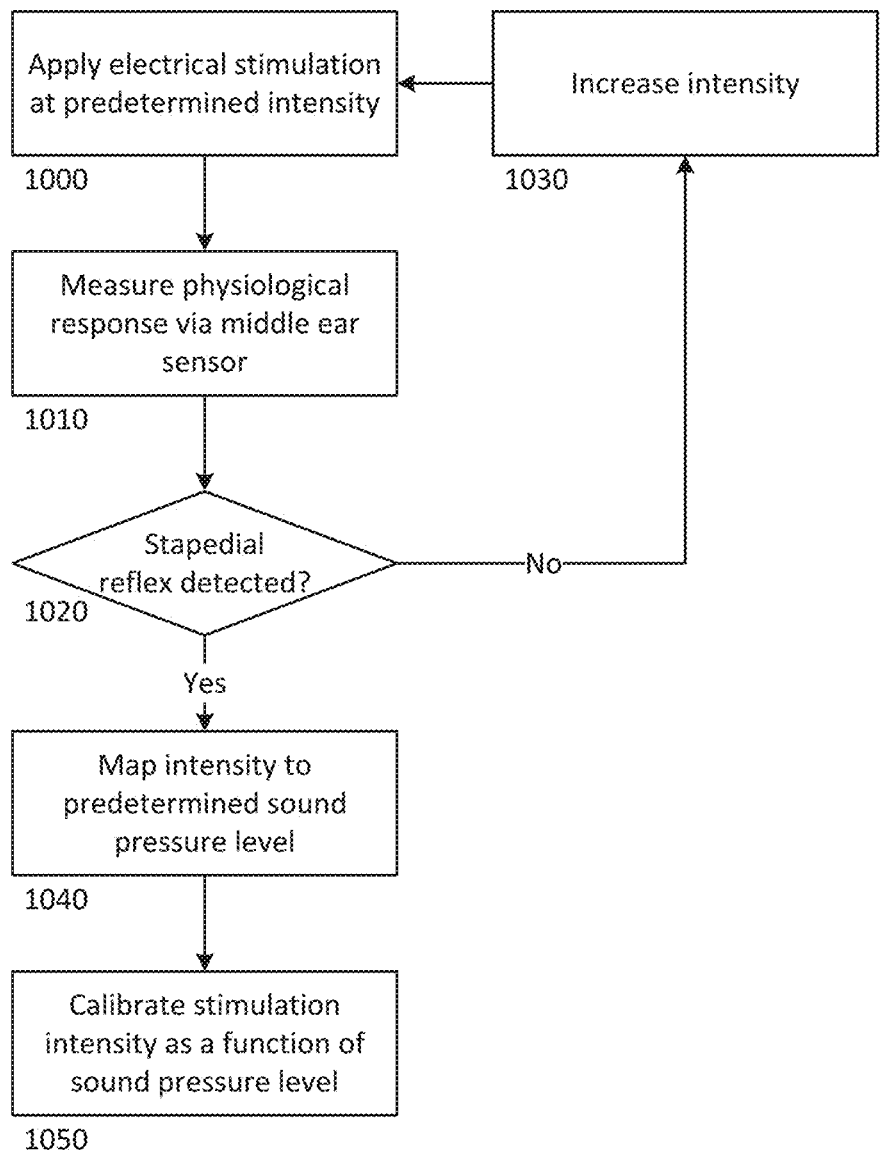
FIG. 10 is a process flow diagram showing an example process for calibrating an implanted system.

FIG. 10 is a process flow diagram showing an example process for calibrating an implanted system. In some examples, one or more sensors (e.g., a sensor contacting the incus such as sensor 310 shown in FIG. 3) can detect a physiological phenomenon known as a stapedial reflex, in which muscles in the middle ear contract in response to various stimuli, such as loud sounds or the expectation of loud sounds. In some examples, an implanted signal processor in communication with such a sensor can recognize the occurrence of a stapedial reflex based on a characteristic output, for instance, via preprogrammed signal recognition or via a learning process, in which the stapedial reflex is triggered and the response from the sensor is measured and learned.

The calibration process of FIG. 10 includes applying electrical stimulation at a predetermined intensity (step 1000) and measuring a physiological response via a middle ear sensor (step 1010). The measured physiological response can be used to detect whether or not a stapedial reflex has occurred (step 1020). If a stapedial reflex is not detected, the intensity of the electrical stimulation is increased (step 1030), and electrical stimulation at the new intensity is applied (step 1000) and the physiological response is measured (step 1010). This process can be repeated until the stapedial reflex is detected at step 1020.

Once the stapedial reflex is detected, the intensity that caused the stapedial reflex can be mapped to a predetermined sound pressure level (step 1040). For instance, in some examples, the lowest electrical intensity determined to cause the detected stapedial reflex can be mapped to an input sound pressure of 100 dB. The method can include calibrating stimulation intensities as a function of sound pressure level (step 1050) based on the mapping of the stapedial reflex-causing intensity to the predetermined sound pressure level.

The calibration process of FIG. 10 can be initiated in a variety of ways. For example, in various embodiments, the process can be initiated by one or more components in communication with the implanted system, such as a programmer, charger, fitting hub, or the like. Such processes can be performed during an initial fitting and/or a calibration after a period of use of the system.

Leveraging fully implanted system and initiating the process via a wireless communication (e.g., from a programmer, fitting hub, another external device, etc.), greatly simplifies the process of triggering and/or detecting the stapedial reflex. For example, utilizing a cochlear electrode (e.g., 916) to cause the stapedial reflex and sensing the reflex using an implanted middle ear sensor eliminates the need for tedious diagnostic equipment such as tympanometry equipment for analyzing a stapedial reflex.

In some examples, the systems and processes described with respect to FIG. 9 can be used in the calibration steps discussed with respect to FIG. 10. For instance, in an illustrative example, the fitting hub 902 of FIG. 9 can cause a speaker 904 to produce a sound having a sound pressure level of 100 dB while also communicating (e.g., via Bluetooth communication) the details of the sound (e.g., intensity, frequency, etc.) to the implantable battery and/or communication module 940. The output of the sensor 910 in response to the 100 dB sound can be identified and associated with the lowest electrical stimulation intensity that causes the detected stapedial reflex. Such a process can be repeated for a plurality of frequencies to link various external acoustic stimuli (e.g., from speaker 904) to particular electrical stimulations. Furthermore, such a process can be performed while an external auditory aid device (e.g. additional auditory aid device 900) is active and/or while the external auditory aid device is inactive such as to link various external acoustic stimuli (e.g., from speaker 904) to particular electrical stimulations such that the electrical stimulations for the various external acoustic stimuli are relatively similar when the external auditory aid device is active or inactive. For example, in some embodiments, the process of FIG. 10 can be performed when an external auditory aid device is active in order to calibrate stimulation intensity as a function of sound pressure level when the external auditory aid device is active. Such calibration can be used to set parameters of a second transfer function to be used when the external auditory aid device is active (e.g., when a cochlear implant system determines via a received status indicator signal that the external auditory aid device is active).

Several embodiments discussed herein generally relate to a cochlear implant system. As discussed herein, cochlear implant systems can comprise a cochlear electrode implanted into the cochlear tissues of a wearer, as well as various other components such as an electrical stimulator, signal processor, and a middle ear sensor. Furthermore, one or more external auditory aid devices may be used in conjunction with the cochlear implant system as described herein. In some embodiments, the cochlear implant system comprises components implanted into one or both sides of a wearer. For example, a system can comprise components implanted in a wearer's left side (e.g. for their left ear), their right side (e.g. for their right ear), or both.

Figure 11:
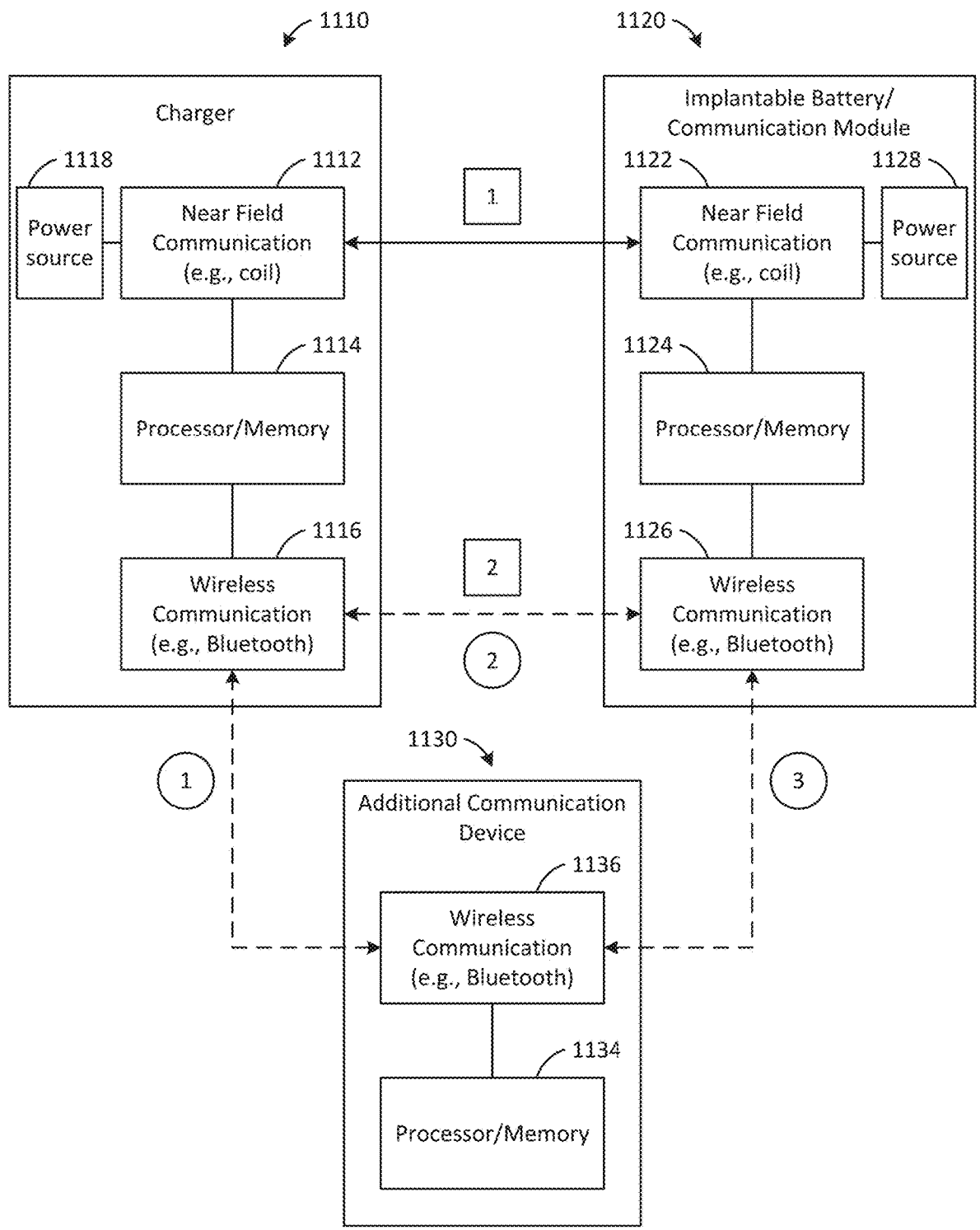
FIG. 11 is a schematic diagram showing establishing a secure wireless connection between various components in an implantable system.

FIG. 11 is a schematic diagram showing establishing a secure wireless connection between various components in an implantable system. In the illustrated example, a charger 1110 is configured to communicate with implantable battery and/or communication module 1120. Charger 1110 includes a wireless communication component 1116, such as a Bluetooth link, that can facilitate communication between the charger 1110 and other devices. Charger 1110 further includes a near field communication component 1112, such as a coil, and a processor/memory component 1114 that can receive signals from and communicate signals to near field communication component 1112 and/or wireless communication component 1116.

Implantable battery and/or communication module 1120 includes a wireless communication component 1126, such as a Bluetooth link, that can facilitate communication between the charger 1110 and other devices. Implantable battery and/or communication module 1120 further includes a near field communication component 1122, such as a coil, and a processor/memory component 1124 that can receive signals from and communicate signals to near field communication component 1122 and/or wireless communication component 1126.

In some embodiments, the near field communication components 1112 and 1122 comprise coils capable of establishing near field wireless communication therebetween. In some embodiments, the coils can also be used to transfer power between a power source 1118 of the charger 1110 to a power source 1128 of the implantable battery and/or communication module 1120, for example, to charge the power source 1128 in the implanted system for continued use. In various embodiments, power source 1118 and/or power source 1128 can include one or more batteries, capacitors (e.g., supercapacitors), and/or other power storage devices that can store and provide electrical energy to other components. In some embodiments, power source 1118 in charger 1110 can include an external or removable power source, such as a removable or replaceable battery and/or a power cord that can be plugged into a standard wall receptacle.

In some examples, implantable battery and/or communication module 1120 is unable to communicate with an external component (e.g. an external fitting hub, an external auditory aid device, or the like) via wireless communication component 1126 until such communication is first enabled. In such embodiments, enabling such communication is performed via near field communication component 1122 to ensure that devices are not accidentally or undesirably paired with the implantable battery and/or communication module 1120.

In the exemplary embodiment of FIG. 11, the numbers in square boxes illustrate an exemplary sequential process for establishing wireless communication between the charger 1110 and the implantable battery and/or communication module 1120. In the illustrated embodiment, charger 1110 first establishes contact with the implantable battery and/or communication module 1120 via near field communication components 1112, 1122. In various embodiments, such near field communication is only operation within very short distances, such as within two inches, for example. This prevents other devices from accidentally or undesirably establishing near field communication with implantable battery and/or communication module 1120. During execution of this step, a user may position the charger 1110 proximate their pectoral region in which the implantable battery and/or communication module 1120 is implanted to enable such communication. In some examples, after pairing the charger 1110 and implantable battery and/or communication module 1120 via near field communication 1112, 1122, such devices can subsequently communicate via wireless communication 1116, 1126. In some examples, such pairing can be performed as described in PCT patent application No. PCT/US20/19166, which is incorporated by reference.

In some embodiments, an external device 1130 (e.g., a smartphone, other audio/media sources, an external auditory aid device, a fitting hub) can include a wireless communication component 1136 and processor/memory 1134 capable of facilitating communication with implantable battery and/or communication module 1120 (e.g., via wireless communication component 1126), but might lack a near field communication component for pairing the external device 1130. Thus, in some examples, the paired charger 1110 can be configured to enable subsequent pairing of the implantable battery and/or communication module 1120 with an external device 1130.

The circled reference numerals show an order of exemplary pairing of external device 1130 with an implantable battery and/or communication module 1120. The charger 1110 can communicate with the external device 1130 via wireless communication components 1116, 1136, for example, to determine that a user wishes to pair the external device 1130 with the implantable battery and/or communication module 1120. The charger 1110 can then communicate with the implantable battery and/or communication module 1120 (e.g., via wireless communication component 1116, 1126) to pair the implantable battery and/or communication module 1120 with the external device 1130 to enable subsequent wireless communication between implantable battery and/or communication module 1120 and the external device 1130 (e.g., via wireless communication component 1126, 1136).

In some examples, once a device is paired with the implantable battery and/or communication module 1120, it can be used to subsequently pair additional devices to the implantable battery and/or communication module as described above with respect to the charger 1110. In other embodiments, only some devices include the ability to pair additional devices with the implantable battery and/or communication module 1120, such as only the charger 1110. In still further examples, every device must be paired with the implantable battery and/or communication module via a near field communication process (e.g., via field communication component 1122) before longer range wireless (e.g., Bluetooth) communication can be established.

Additionally or alternatively, once an external device is paired with the implantable battery and/or communication module 1120, the external device (e.g. external device 1130) may be used to perform additional functions. In some embodiments, the additional functions may comprise adjusting one or more transfer functions of the signal processor. In some examples, the external device includes or otherwise communicate with one or more sensors and can be configured to update a transfer function of the signal processor based on one or more signals detected via the one or more sensors. In some such examples, one or more such sensors can include a microphone, a location sensor (e.g. GPS, location based on one or more available wireless networks, etc.), a clock, or other sensors known to one of ordinary skill in the art. In some embodiments, external device (e.g., 1130) including or in communication with such one or more sensors includes a smartphone, tablet, computer, or external auditory aid device.

In embodiments wherein the external device includes, or is in communication with, a microphone, the external device can be configured to reprogram the signal processor based on information collected from the microphone representative of the acoustic environment. For example, the external device can be configured to identify background noise (e.g. low-end noise) and update one or more transfer functions accordingly. In some such examples, the external device can be configured to reduce gain for low-end signals and/or emphasize other sounds or frequency ranges, such as speech or other sounds having a higher frequency. In some embodiments, a user can initiate the process of identifying background noise for adjusting the operation of the signal processor via the external device, for example, via a user interface (e.g., a smartphone or tablet touchscreen).

In embodiments in which the external device includes or is in communication with a location sensor and/or a clock, the external device may reprogram the signal processor based on a detected location and/or time. For instance, in an example embodiment, when the external device is located in a place known to be loud (e.g. a mall or sports stadium), the external device can be configured to detect the location and automatically reprogram the signal processor to reduce background noise (e.g., a particular frequency or range of frequencies) and/or reduce the overall gain associated with a transfer function. Similarly, in some examples, when located in a place in which a wearer may wish to particularly recognize speech (e.g., a movie theater) the external device can be configured to reprogram the signal processor to emphasize frequencies associated with speech.

In some examples, one or more transfer functions can be updated to reduce a contribution of identified background noise. In some embodiments, reducing a contribution of identified background noise comprises emphasizing signals having frequency content between approximately 200 Hz and 20 kHz. In some such examples, updating a transfer function to reduce a contribution of the identified background noise comprises emphasizing signals having frequency content between approximately 300 Hz and 8 kHz. Emphasizing signals in such frequency ranges can help emphasize human speech or other similar signals within a noisy environment.

Additionally or alternatively, the external device can be configured to reprogram the signal processor based on a determined time of day. For example, at times when the wearer generally doesn't want to be bothered (e.g. at night), the external device can be configured to lower the volume of all or most sounds. In some examples, the wearer may additionally or alternatively temporarily reprogram the signal processor via the external device to adjust one or more transfer functions of the signal processor (e.g., to reduce volume) for a predetermined amount of time (e.g. 15 minutes, 1 hour, or 1 day).

In some examples, reprogramming the signal processor comprises adjusting a transfer function to effect a relative change (e.g., reduce volume). In some cases, reprogramming the signal processor comprises implementing a predefined transfer function in response to received data, such as location data indicating the wearer is in a particular location. In some such examples, a plurality of pre-programmed transfer functions are stored in a memory and can be implemented based on data acquired via one or more sensors of the external device and/or the activity of one or more external auditory aid devices.

In some embodiments, the external device can be configured to provide an input signal based on audio generated by the external device. For example, the external device can be a smartphone, and can provide an input signal to a wearers implantable battery and/or communication module comprising audio from a phone call, text to speech audio (e.g. reading a text message or an article out loud), and/or media audio (e.g. videos, music, games, etc.). The implantable battery and/or communication module can be configured to relay the input signal to the signal processor for the signal processor to convert into corresponding stimulation signals.

With reference back to FIG. 11, in various embodiments, once a device (e.g., charger 1110, external device 1130, etc.) has been paired with the implantable battery and/or communication module 1120 for wireless communication, information associated with the pairing (e.g., device identifiers, etc.) can be stored in one or more memory components (e.g., 1114, 1124, 1134) so that the pairing need not be performed again in the future. In some embodiments, one or more devices can be unpaired from communication with the implantable battery and/or communication module 1120. For instance, the device can be used to disconnect from the implantable battery and/or communication module 1120 if the device is no longer being used by the user (e.g., discarded, returned, given away, etc.). Additionally or alternatively, a device can be automatically unpaired if the device has not established wireless communication with the implantable battery and/or communication module 1120 within a certain amount of time since the last connection. For instance, in an exemplary embodiment, if a device transmitting a Bluetooth audio stream to an implanted system via the implantable battery and/or communication module becomes disconnected from the implantable battery and/or communication module for greater than 5 minutes, the device becomes unpaired from the implantable battery and/or communication module and must be re-paired for future use.

Pairing processes described herein can be used to establish communication between and external auditory aid device and a cochlear implant system. Such communication can be used to communicate a status indicator signal from the external auditory aid device to the cochlear implant system such as described herein. Additionally or alternatively, in some examples, communication between an external auditory aid device and a cochlear implant system can be established via a pairing device, such as described in U.S. patent application Ser. No. 17/006,467, filed Aug. 28, 2020, and entitled PROGRAMMING OF COCHLEAR IMPLANT ACCESSORIES, which is incorporated herein by reference.

While several embodiments described herein include receiving a status indicator signal via the cochlear implant system, in some examples, the status indicator signal can be received by an external control device in communication with the cochlear implant system. In some such examples, an external control device (e.g., a programmer or charger) in communication with the cochlear implant system can receive a status indicator signal representative of operation of an external auditory aid device. The external control device can communicate with the cochlear implant system to update the transfer function based on the received status indicator signal such as via processes similar to those discussed herein.

Various non-limiting embodiments have been described. These and others are within the scope of the following claims.

The invention claimed is:

1. A method of operating an implantable cochlear implant system, comprising:
   receiving a stimulus via an input source of a cochlear implant system;
   generating one or more input signals representative of the received stimulus;
   receiving the one or more input signals via an implanted signal processor of the cochlear implant system and outputting a stimulation signal to a stimulator of the cochlear implant system based on the received one or more input signals and a transfer function associated with the implanted signal processor of the cochlear implant system;
   detecting an active external auditory aid device that affects the stimulus received via the input source and the one or more input signals representative of the received stimulus; and
   updating the transfer function of the implanted signal processor to compensate for operation of the external auditory aid device.

2. The method of claim 1, wherein updating the transfer function of the implanted signal processor to compensate for operation of the external auditory aid device comprises changing from a first operating profile of the cochlear implant system having a first associated transfer function to a second operating profile of the cochlear implant system having a second associated transfer function.

3. The method of claim 2, further comprising receiving information regarding one or more operating characteristics of the external auditory aid device; and
   wherein the second operating profile is based on the one or more operating characteristics of the external auditory aid device.

4. The method of claim 1, wherein updating the transfer function of the implanted signal processor to compensate for operation of the external auditory aid device comprises adjusting the transfer function based on a gain profile of the external auditory aid device.

5. The method of claim 1, wherein the external auditory aid device comprises an external hearing aid.

6. A method of operating an implantable cochlear implant system, comprising:
   receiving a stimulus via an input source of a cochlear implant system;
   generating one or more input signals representative of the received stimulus;
   receiving the one or more input signals via an implanted signal processor of the cochlear implant system and outputting a stimulation signal to a stimulator of the cochlear implant system based on the received one or more input signals and a transfer function associated with the implanted signal processor of the cochlear implant system; and
   upon a turning on of an external auditory aid device that affects the stimulus received via the input source and the one or more input signals representative of the received stimulus, updating the transfer function of the implanted signal processor to compensate for operation of the external auditory aid device.

7. The method of claim 6, wherein updating the transfer function of the implanted signal processor to compensate for the operation of the external auditory aid device comprises:
   updating the implanted signal processor transfer function from a first transfer function to a second transfer function so that the stimulation signal output to the stimulator is based on the received one or more input signals and the updated transfer function, wherein the first transfer function is different than the second transfer function.

8. The method of claim 6, further comprising receiving a status indicator signal to the cochlear implant system indicating that the external auditory aid device is active, and wherein updating the transfer function of the implanted signal processor to compensate for operation of the external auditory aid device is in response to the received status indicator signal.

9. The method of claim 8, further comprising outputting, by an external control device, a wireless communication comprising the status indicator signal so that receiving the status indicator signal comprises receiving a wireless communication output from the external control device indicating that the external auditory aid device is active.

10. The method of claim 9, wherein the status indicator signal is manually sent by a user via the external control device.

11. The method of claim 10, further comprising receiving, from the external control device, one or more operating parameters of the external auditory aid device.

12. The method of claim 6, further comprising disabling an automatic gain control (AGC) function of the cochlear implant system.

13. The method of claim 6, further comprising disabling an automatic gain control (AGC) function of the external auditory aid device.

14. The method of claim 6, wherein updating the transfer function of the implanted signal processor to compensate for operation of the external auditory aid device comprises changing from a first operating profile having a first associated transfer function to a second operating profile having a second associated transfer function.

15. The method of claim 6, further comprising testing an efficacy of the updated transfer function.

16. The method of claim 15, further comprising testing an efficacy of each of a plurality of transfer functions compensating for operation of the external auditory aid device.

17. The method of claim 16, further comprising selecting or creating a preferred transfer function based on the testing the efficacy of the plurality of transfer functions.

18. The method of claim 6, further comprising:
pairing the external auditory aid device and the cochlear implant system via a Bluetooth communication link; and
receiving a status indicator signal indicating that the external auditory aid device is active via the Bluetooth communication link and updating the transfer function in response to the received status indicator signal.

19. The method of claim 18, wherein the received status indicator signal comprises one or more external auditory aid device operating parameters, and wherein updating the transfer function is based on the one or more external auditory aid device operating parameters.

20. The method of claim 6, wherein the external auditory aid device comprises an external hearing aid.

\* \* \* \* \*